US012685544B2

(12) United States Patent
Wong et al.

(10) Patent No.: US 12,685,544 B2
(45) Date of Patent: Jul. 21, 2026

(54) MINIMALLY INVASIVE GUIDES AND CUTTING INSTRUMENTS

(71) Applicant: WRIGHT MEDICAL TECHNOLOGY, INC., Memphis, TN (US)

(72) Inventors: Kian-Ming Wong, Lakeland, TN (US); Brian Robert Thoren, Memphis, TN (US); Shawn McGinley, Arlington, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 440 days.

(21) Appl. No.: 18/488,185

(22) Filed: Oct. 17, 2023

(65) Prior Publication Data

US 2024/0041477 A1 Feb. 8, 2024

Related U.S. Application Data

(60) Continuation of application No. 17/643,859, filed on Dec. 13, 2021, now Pat. No. 11,819,187, which is a
(Continued)

(51) Int. Cl.
*A61B 17/17* (2006.01)
*A61B 17/00* (2006.01)
*A61F 2/30* (2006.01)

(52) U.S. Cl.
CPC ........ *A61B 17/17* (2013.01); *A61B 17/00234* (2013.01); *A61F 2002/30622* (2013.01)

(58) Field of Classification Search
CPC ............... A61B 17/17; A61B 17/00234; A61F 2002/30622
See application file for complete search history.

(56) References Cited

U.S. PATENT DOCUMENTS 6,796,986 B2    9/2004   Duffner
8,388,690 B2    3/2013   Singhatat
(Continued)

FOREIGN PATENT DOCUMENTS

GB        2480846 A      12/2011
JP    2004298259 A      10/2004
(Continued)

OTHER PUBLICATIONS

First Examination Report issued in connection with Australian Patent Application No. 2019341065, Jun. 20, 2020, 3 pages.
(Continued)

*Primary Examiner* — Sameh R Boles
(74) *Attorney, Agent, or Firm* — DUANE MORRIS LLP

(57) ABSTRACT

A surgical guide includes a first guide arm extending from a first end to a second end on a first longitudinal axis. The first guide arm defines a first plurality of openings sized and configured to receive a first guide element therethrough. A second guide arm extends from a first end to a second end on a second longitudinal axis. The second guide arm defines a second plurality of openings sized and configured to receive a second guide element therethrough. A pivot element couples the first end of the first guide arm to the first end of the second guide arm such that an angular distance between the first guide arm and the second guide arm can be adjusted in a first plane.

18 Claims, 18 Drawing Sheets

Related U.S. Application Data division of application No. 16/648,861, filed as application No. PCT/US2019/044587 on Aug. 1, 2019, now Pat. No. 11,229,443.

(60) Provisional application No. 62/774,385, filed on Dec. 3, 2018.

(56)                     References Cited

U.S. PATENT DOCUMENTS

| | | | |
|---|---|---|---|
| 8,475,462 | B2 | 7/2013 | Thomas et al. |
| 2002/0165552 | A1 | 11/2002 | Duffner |
| 2005/0055028 | A1* | 3/2005 | Haines ................. A61B 17/155 |
| | | | 606/79 |
| 2005/0273112 | A1 | 12/2005 | McNamara |
| 2009/0254126 | A1 | 10/2009 | Orbay et al. |
| 2009/0306679 | A1 | 12/2009 | Murphy |
| 2010/0087824 | A1 | 4/2010 | Collazo |
| 2010/0191243 | A1 | 7/2010 | Horan et al. |
| 2013/0282016 | A1 | 10/2013 | Volpi et al. |
| 2014/0142582 | A1 | 5/2014 | Biedermann et al. |
| 2014/0188139 | A1 | 7/2014 | Fallin et al. |
| 2016/0030065 | A1 | 2/2016 | Claes et al. |
| 2016/0235414 | A1 | 8/2016 | Hatch et al. |
| 2017/0049462 | A1 | 2/2017 | Walton |
| 2017/0056031 | A1 | 3/2017 | Awtrey et al. |

FOREIGN PATENT DOCUMENTS

| | | |
|---|---|---|
| JP | 2012515623 A | 7/2012 |
| JP | 201497383 A | 5/2014 |
| JP | 2014204970 A | 10/2014 |
| WO | 2016054262 A2 | 4/2016 |

OTHER PUBLICATIONS

Office Action issued in connection with corresponding Canadian Patent Application No. 3,076,066, Sep. 21, 2021, 4 pages.
International Search Report and Written Opinion issued in connection with corresponding International Patent Application No. PCT/US2019/044587, 14 pages, Oct. 17, 2019.
First Examination Report issued in connection with corresponding Australian Patent Application No. 2020250315, Feb. 25, 2021, 3 pages.
Office Action issued in connection with corresponding Japanese Patent Application No. 2020-516829, May 3, 2021, 3 pages.
Partial Supplementary European Search Report issued in connection with European Patent Application No. 19892296.5, Jul. 20, 2022, 14 pages.
Extended European Search Report issued in connection with European Patent Application No. 19892296.5, Oct. 21, 2022, 13 pages.

\* cited by examiner

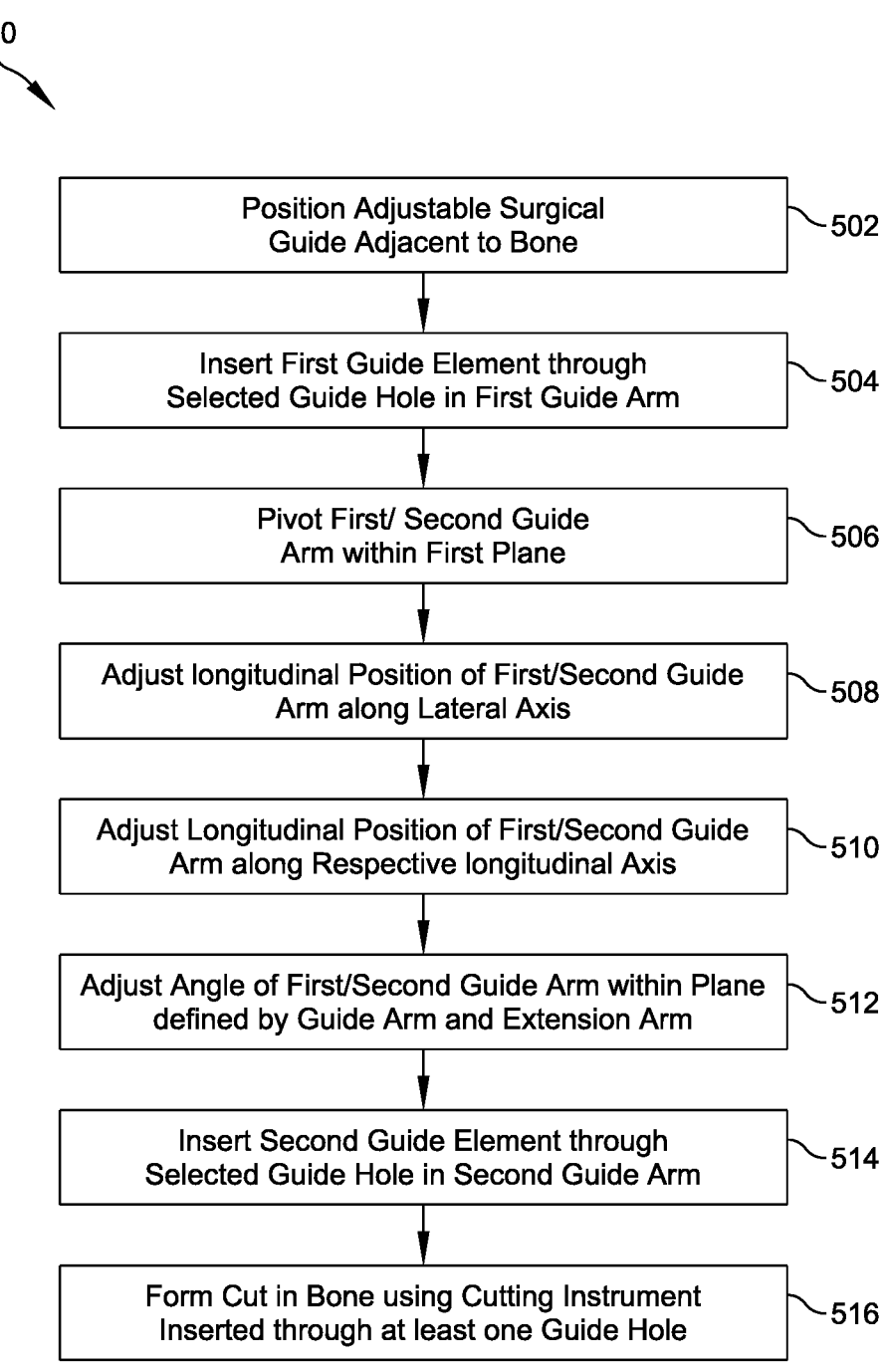

500

Position Adjustable Surgical
Guide Adjacent to Bone — 502

Insert First Guide Element through
Selected Guide Hole in First Guide Arm — 504

Pivot First/ Second Guide
Arm within First Plane — 506

Adjust longitudinal Position of First/Second Guide
Arm along Lateral Axis — 508

Adjust Longitudinal Position of First/Second Guide
Arm along Respective longitudinal Axis — 510

Adjust Angle of First/Second Guide Arm within Plane
defined by Guide Arm and Extension Arm — 512

Insert Second Guide Element through
Selected Guide Hole in Second Guide Arm — 514

Form Cut in Bone using Cutting Instrument
Inserted through at least one Guide Hole — 516

Position Adjustable Surgical
Guide Adjacent to Bone          ~502

Insert First Guide Element
through Selected Guide Hole          ~504

Pivot First/ Second Guide
Arm within First Plane          ~506

Adjust Position of Slideable Guide Element
within Slot Defined by Guide Arm          ~530

Form Cut in Bone using Cutting Instrument
Inserted through at least one Guide Hole          ~516

MINIMALLY INVASIVE GUIDES AND CUTTING INSTRUMENTS

CROSS-REFERENCE TO RELATED APPLICATIONS

This is a continuation of U.S. patent application Ser. No. 17/643,859, filed Dec. 13, 2021, which is a divisional of U.S. patent application Ser. No. 16/648,861, filed Mar. 19, 2020 (U.S. Pat. No. 11,229,443), which is a national stage patent application, filed under 35 U.S.C. 371, of International Patent Application No. PCT/US2019/044587, filed Aug. 1, 2019, which claims priority to U.S. Provisional Patent Application No. 62/774,385, filed Dec. 3, 2018, the entireties of which are incorporated by reference herein.

FIELD OF THE INVENTION

This disclosure relates generally to surgical guides and methods of use for minimally invasive surgery and, more specifically, to surgical guides and methods of use for Charcot minimally invasive surgery.

BACKGROUND

Arthrodesis refers to surgical fixation of a joint, ultimately resulting in bone fusion. An arthrodesis procedure induces ankylosis performed to relieve pain or provide support in a diseased or injured joint. Tibiotalocalcaneal ("TTC") or tibiocalcaneal ("TC") arthrodesis is a salvage procedure for the treatment of joint disease or pain and dysfunction due to arthritic ankle and subtalar joints, e.g., Charcot disease. In performing ankle and subtalar arthrodesis, the surgeon may wish to achieve anatomic alignment, pain relief, and a stable, plantigrade foot. Secure fixation while preserving the surrounding soft tissue can also contribute to a successful outcome.

Anatomic alignment, pain relief, stabilization, or other desired surgical outcomes may require cutting or other bone removal to form a cavity, wedge, or other space within or between bones for alignment and repositioning of the bones. Accurate positioning and formation of cuts in the bones is essential for ensuring proper relief and treatment of Charcot disease or other arthrodesis. Current systems for forming cuts present infection risks, slow tissue healing, and requires the use of frames and/or burrs that is time consuming and requires long incision paths.

SUMMARY

In some embodiments, a surgical guide is disclosed. The surgical guide includes a first guide arm extending from a first end to a second end on a first longitudinal axis. The first guide arm defines a first plurality of openings sized and configured to receive a first guide element therethrough. A second guide arm extends from a first end to a second end on a second longitudinal axis. The second guide arm defines a second plurality of openings sized and configured to receive a second guide element therethrough. A pivot element couples the first end of the first guide arm to the first end of the second guide arm such that an angular distance between the first guide arm and the second guide arm can be adjusted in a first plane.

In various embodiments, a surgical method is disclosed. The surgical method includes a step of positioning a surgical guide adjacent to a bone. The surgical guide includes a first guide arm extending substantially on a first longitudinal axis and defining a first plurality of openings, a second guide arm extending substantially on a second longitudinal axis and defining a second plurality of openings, and a pivot element coupling the first guide arm to the second guide arm. A first guide element is inserted through a selected one of the first plurality of openings defined by the first guide arm. The first guide arm and the second guide arm are pivoted about the pivot element to adjust an angular distance between the first guide arm and the second guide arm. A second guide element is inserted through a selected one of the second plurality of openings defined by the second guide arm. A wedge osteotomy is formed in the bone. The first guide element and the second guide element are configured to position a cutting guide for forming the wedge osteotomy.

In various embodiments, a surgical guide is disclosed. The surgical guide includes a first guide arm extending from a first end to a second end on a first longitudinal axis. The first guide arm defines a first plurality of openings sized and configured to receive a first guide element therethrough. A second guide arm extends from a first end to a second end on a second longitudinal axis. The second guide arm defines a second plurality of openings sized and configured to receive a second guide element therethrough. A first slide element is coupled to the first end of the first guide arm. A first extension element extends from a first end to a second end on a third longitudinal axis and defining a first adjustment slot extending substantially on the third longitudinal axis. The first slide element is positioned at least partially within the first slot and is slideable on the third longitudinal axis. A second slide element coupled to the first end of the second guide arm. A second extension element extends from a first end to a second end on a fourth longitudinal axis and defines a second adjustment slot extending substantially on the fourth longitudinal axis. The second slide element is positioned at least partially within the second slot and is slideable on the fourth longitudinal axis. A pivot element couples the first end of the first extension element to the first end of the second extension element such that an angular distance between the first guide arm and the second guide arm can be adjusted in a first plane.

BRIEF DESCRIPTION OF THE FIGURES

The features and advantages of the present invention will be more fully disclosed in, or rendered obvious by the following detailed description of the preferred embodiments, which are to be considered together with the accompanying drawings wherein like numbers refer to like parts and further wherein:

FIG. 17 is a flowchart illustrating a method of forming a cut in a bone using an adjustable surgical guide, in accordance with some embodiments.

DETAILED DESCRIPTION

Figure 1:
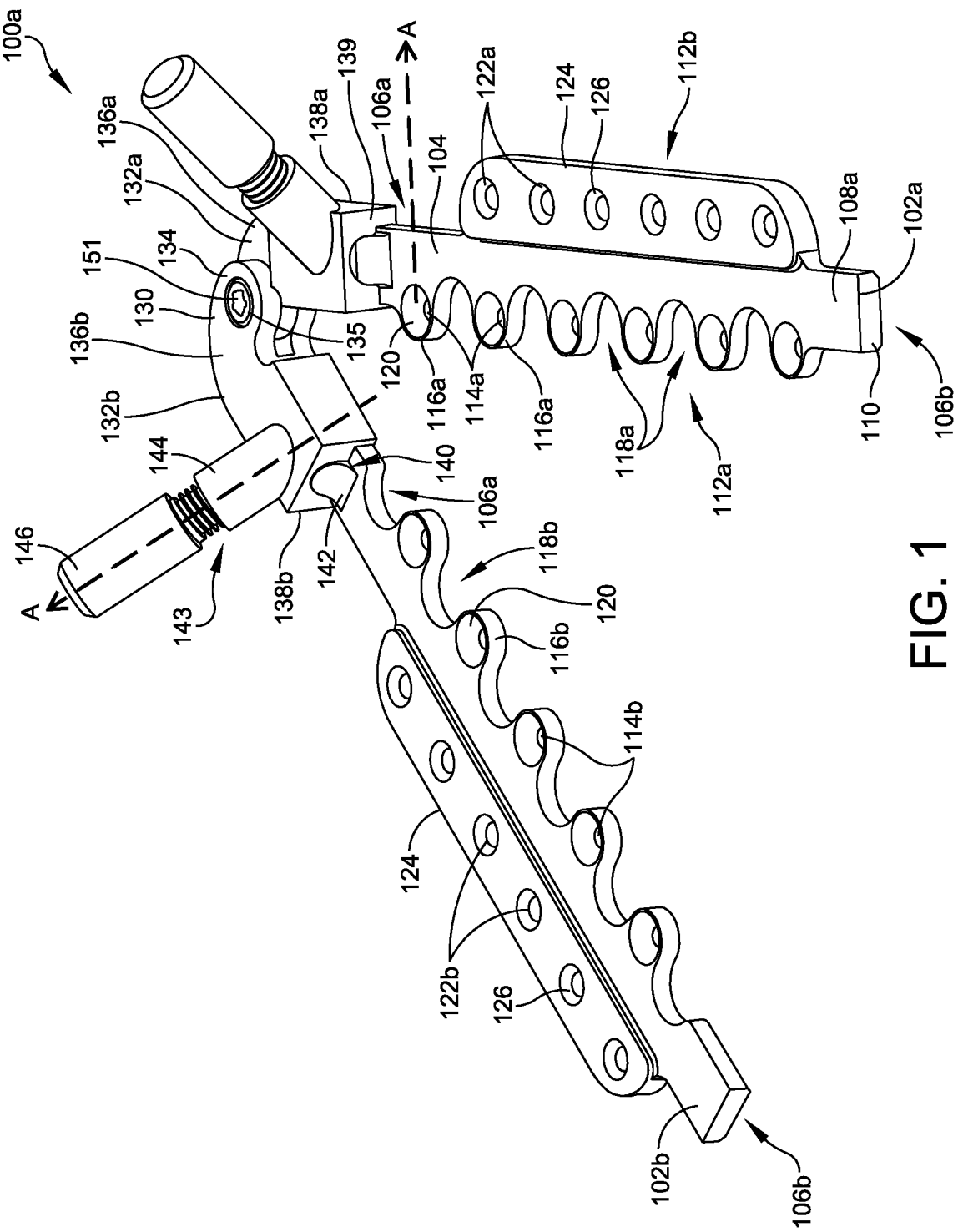
FIG. 1 illustrates an isometric view an adjustable surgical guide, in accordance with some embodiments
Figure 2:
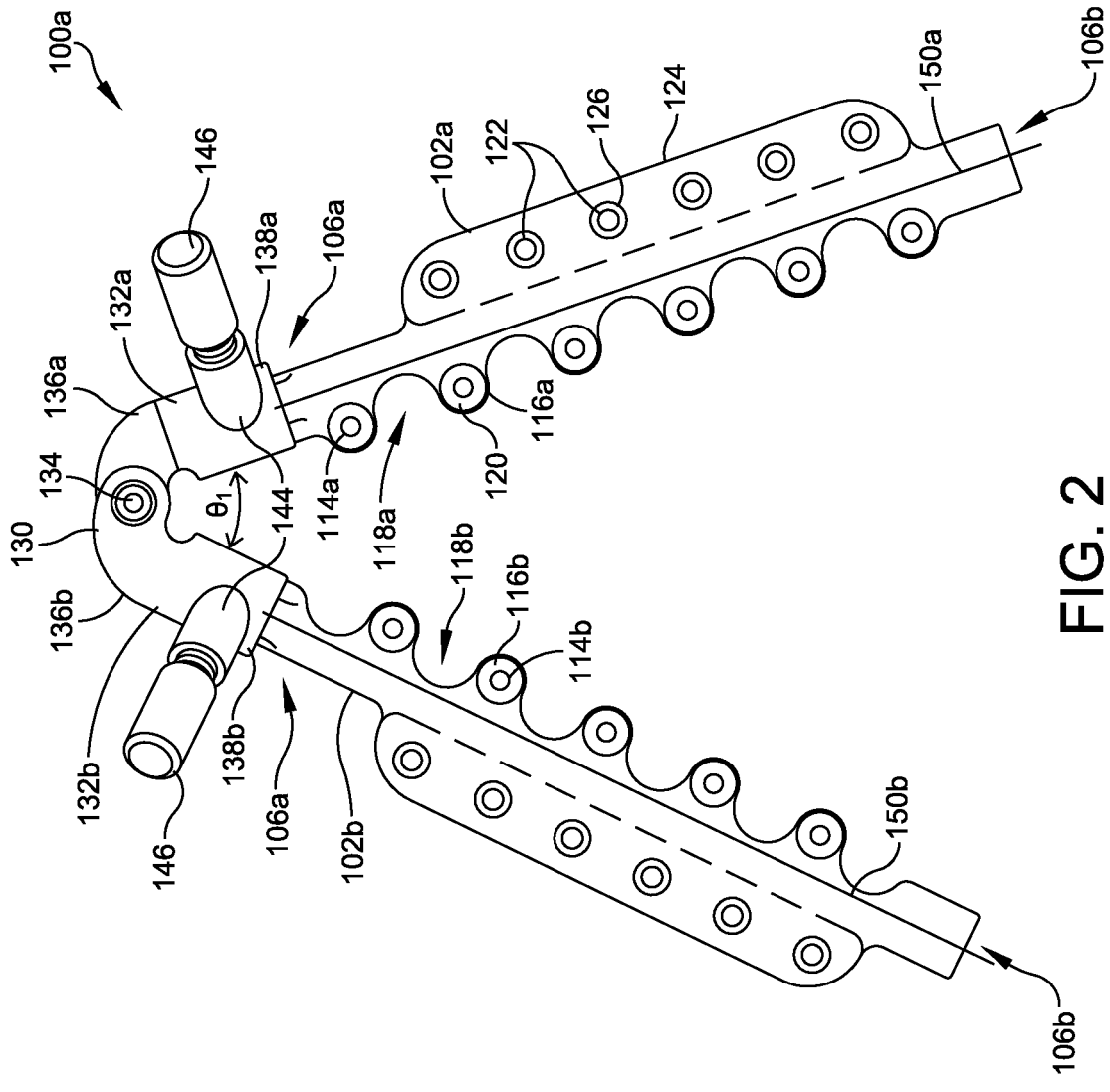
FIG. 2 illustrates a top view of the adjustable surgical guide of FIG. 1, in accordance with some embodiments.
Figure 3:
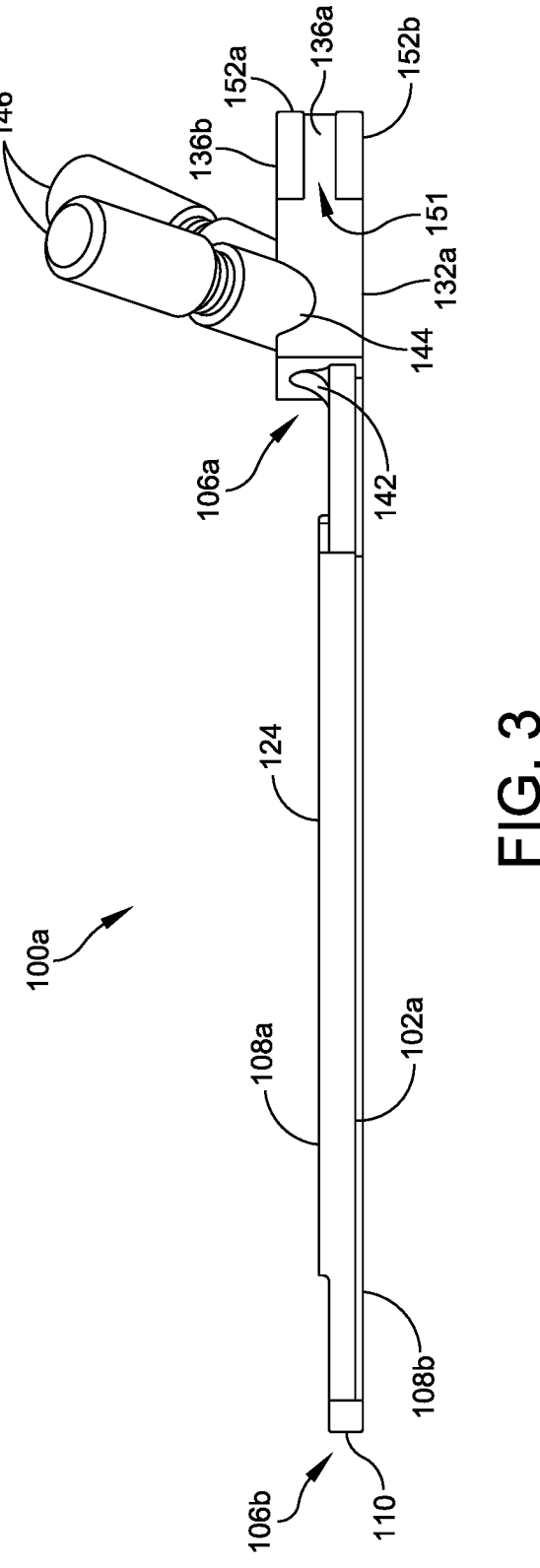
FIG. 3 illustrates a side view of the adjustable surgical guide of FIG. 1, in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top," "bottom," "proximal," "distal," "superior," "inferior," "medial," and "lateral" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise. Like elements have been given like numerical designations to facilitate an understanding of the present subject matter.

As used herein, the term "substantially" denotes elements having a recited relationship (e.g., parallel, perpendicular, aligned, etc.) within acceptable manufacturing tolerances. For example, as used herein, the term "substantially parallel" is used to denote elements that are parallel or that vary from a parallel arrangement within an acceptable margin of error, such as +/−5°, although it will be recognized that greater and/or lesser deviations can exist based on manufacturing processes and/or other manufacturing requirements.

In various embodiments, a surgical guide is disclosed. The surgical guide includes a first guide arm extending from a first end to a second end along a first longitudinal axis. The first guide arm defines a first plurality of openings sized and configured to receive a first guide element therethrough. A second guide arm extends from a first end to a second end along a second longitudinal axis. The second guide arm defines a second plurality of openings sized and configured to receive a second guide element therethrough. A pivot element couples the first end of the first guide arm to the first end of the second guide arm such that an angle between the first guide arm and the second guide arm can be adjusted in a first plane.

FIGS. 1-4 illustrate an adjustable surgical guide 100a, in accordance with some embodiments. The surgical guide 100a includes a first guide arm 102a and a second guide arm 102b. Each of the guide arms 102a, 102b includes a body 104 extending between a proximal end 106a and a distal end 106b substantially along a longitudinal axis 150a, 150b. The body 104 of each guide arm 102a, 102b further extends between an upper surface 108a and a lower surface 108b and is defined by a perimeter wall 110. The perimeter wall 110 can define any suitably shape, such as, for example, a rectangular perimeter, an oval perimeter, etc. In some embodiments, a guide block 124 is coupled to an outer perimeter wall 112b of the body 104 of each of the guide arms 102a, 102b.

In some embodiments, each of the guide arms 102a, 102b defines a plurality of guide holes 114a, 114b extending from the upper surface 108a to the lower surface 108b. For example, in the illustrated embodiment, the first guide arm 102a defines a first plurality of guide holes 114a arranged parallel to the first longitudinal axis 150a and the second guide arm 102b defines a second plurality of guide holes 114b arranged parallel to the second longitudinal axis 150b. Although specific embodiments are illustrated, it will be appreciated that the first and second plurality of guide holes 114a, 114b can extend through any suitable portion of respective first and second guide arms 102a, 102b. The guide holes 114a, 114b are each sized and configured to receive a guide element, such as a k-wire, a screw, etc., therethrough. The guide element provides a reference point for one or more additional guides, such as a cutting guide, couple to the guide element for subsequent surgical procedures.

In some embodiments, each of the guide holes 114a, 114b are defined by a guide extension 116a, 116b extending from an inner surface 112a of the body 104. The guide extensions 116a, 116b define bumps (or peaks) extending from the body 104. In some embodiments, each of the guide extensions 116a, 116b defines a sloped guide surface 120 surrounding the guide hole 114a, 114b to guide a cutting element, such as a k-wire or burr, into the guide hole 114a, 114b. In some embodiments, the guide extensions 116a, 116b are alternated with cutouts 118a, 118b (or valleys). The guide extensions 116a of the first guide arm 102a are sized and positioned to fit within the cutouts 118b of the second guide arm 102b. Similarly, the guide extensions 116b of the second guide arm 102b are sized and positioned to fit within the cutouts 118a of the first guide arm 102b. The guide extensions 116a, 116b and the cutouts 118a, 118b allow the guide arms 102a, 102b to be interlocked in a flush arrangement.

In some embodiments, the first guide arm 102a includes a third plurality of guide holes 122a and/or the second guide arm 102b includes a fourth plurality of guide holes 122b. The guide holes 122a, 122b extend from the first surface 108a to the second surface 108b through a guide block 124 extending from an outer perimeter surface 112b of the body 104. Each of the guide holes 122a, 122b is sized and configured to receive a fixation element, such as a k-wire, therethrough. The guide holes 122a, 122b are configured to guide the fixation element to a predetermined position on the bone. In some embodiments, the guide holes 122a, 122b are positioned on an axis substantially parallel to and offset from the longitudinal axis 150a, 150b and/or the first/second plurality of holes 114a, 114b of the respective guide arm 102a, 102b, although it will be appreciated that the guide holes 122a, 122b may be arranged in any pattern and extend through any portion of the guide body 104 and/or the guide block 124.

In some embodiments, the first guide arm 102a is coupled to the second guide arm 102b by a pivot element 130. The pivot element 130 is configured to limit respective movement of the first guide arm 102a and the second guide arm 102b to a single plane, such as, for example, a first plane intersecting (e.g., defined by) each of the longitudinal axes 150a, 150b. In some embodiments, the pivot element 130 is configured to allow movement of the first guide arm 102a with respect to the second guide arm 102b to adjust an angle $\Theta_1$ defined in the first plane between the first guide arm 102a and the second guide arm 102b. The angle $\Theta_1$ may be adjusted from a minimum angle to a maximum angle. For example, in some embodiments, the first guide arm 102a and the second guide arm 102b may be adjusted from a minimum angle of 0° (i.e., the first guide arm 102a aligned in the same direction as the second guide arm 102b) to a maximum angle of 180° (i.e., the first guide arm 102a aligned in an opposite direction as the second guide arm 102b). Although specific embodiments are discussed herein, it will be appreciated that the pivot element 130 can be configured to continuously and/or discretely adjust the angle $\Theta_1$ within any predetermined range, such as, for example, 0-90°, 0-180°, 0-270°, 0-360°, and/or any other suitable range of angles.

In some embodiments, the pivot element 130 includes a first pivot arm 132a and a second pivot arm 132b coupled by a pin 134. The first pivot arm 132a and the second pivot arm 132b are pivotally coupled such that an angle (e.g., $\Theta_1$) between the first pivot arm 132a and the second pivot arm 132b can be adjusted. For example, in the illustrated embodiment, the first pivot arm 132a includes a first coupling portion 136a sized and configured to fit within a second coupling portion 136b of the second pivot arm 132b. The second coupling portion 136b defines a first arm 152a spaced apart from a second arm 152b to define a coupling channel 142 therebetween. The coupling channel 142 is sized and configured to receive the first coupling portion 136a therein. When the first coupling portion 136a is positioned between the first and second arms 152a, 152b of the second coupling portion 136b, pin holes 151 defined in each of the first and second coupling portions 136a, 136b are aligned. The pin holes 151 are sized and configured to receive a pin 134 therein. The pin 134 couples the first coupling portion 136a to the second coupling portion 136b in a pivoting (or hinged) engagement. Although specific embodiments are discussed herein, it will be appreciated that any suitable coupling mechanism that provides pivoting movement of the first pivot arm 132a with respect to the second pivot arm 132b may be used, and is within the scope of this disclosure. In some embodiments, the pivot element 130 defines at least one hole (not shown) extending therethrough sized and configured to receive a k-wire, burr, or other element therethrough.

Each of the pivot arms 132a, 132b define a guide connection portion 138a, 138b coupled to and/or formed integrally with the respective first and second coupling elements 136a, 136b. The guide connection portions 138a, 138b each define a channel or opening 140 extending from a first surface 139 into the guide connection portion 138a, 138b. The channel 140 is sized and configured to receive a portion of a respective guide arm 102a, 102b therein. In some embodiments, the guide arm 102a, 102b is coupled to the guide connection portion 138a, 138b by a releasable locking mechanism 143. For example, in the illustrated embodiment, the releasable locking mechanism 143 includes an extension 144 extending from the guide connection portion 138a, 138b and defining a channel 153 therethrough. The channel 153 extends into and intersects the channel 140 extending into the guide connection portion 138a, 138b. The interior surface of the channel 153 is threaded. A locking element 144 is positioned at least partially within the channel 153.

Figure 4:
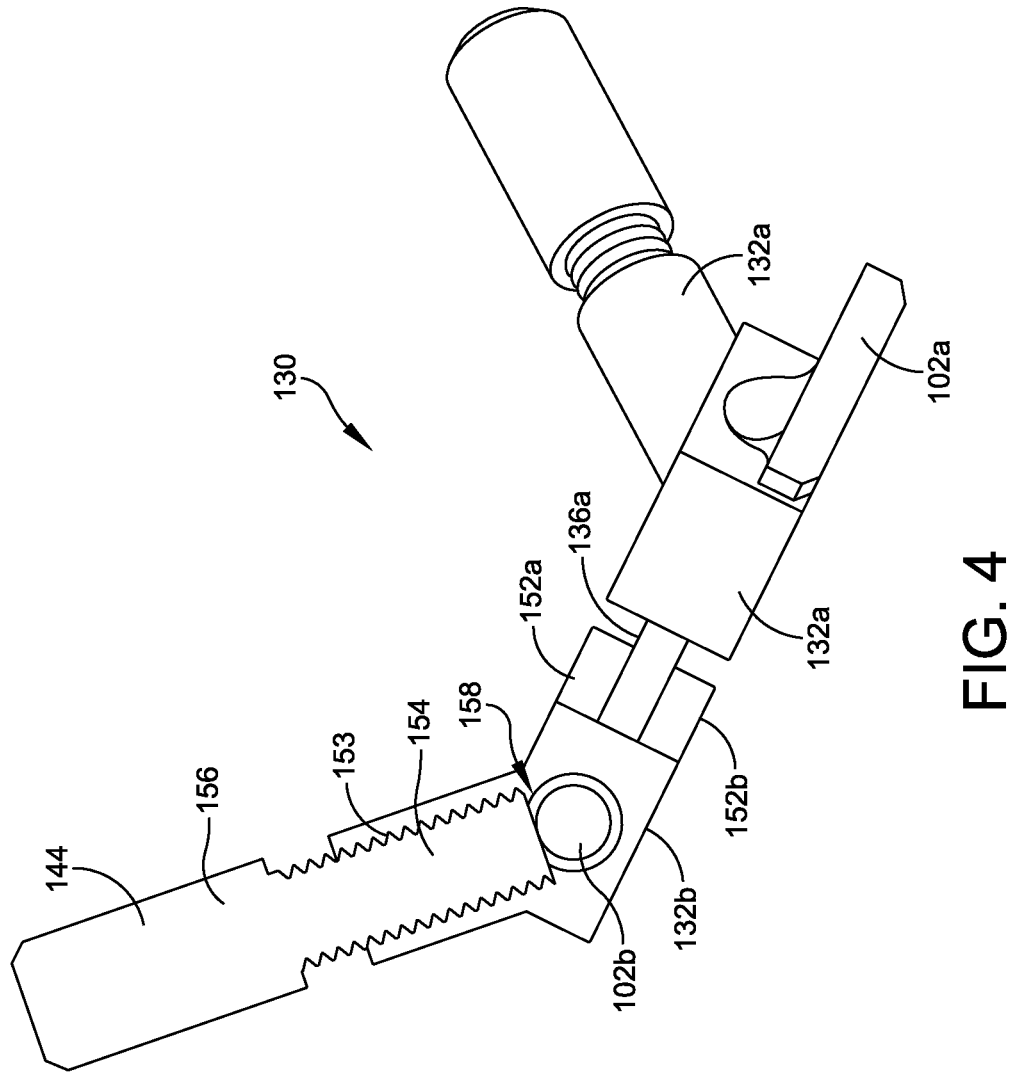
FIG. 4 illustrates a cross-sectional view of a pivot element of the adjustable surgical guide of FIG. 1 taken along line A-A, in accordance with some embodiments.
Figure 5:
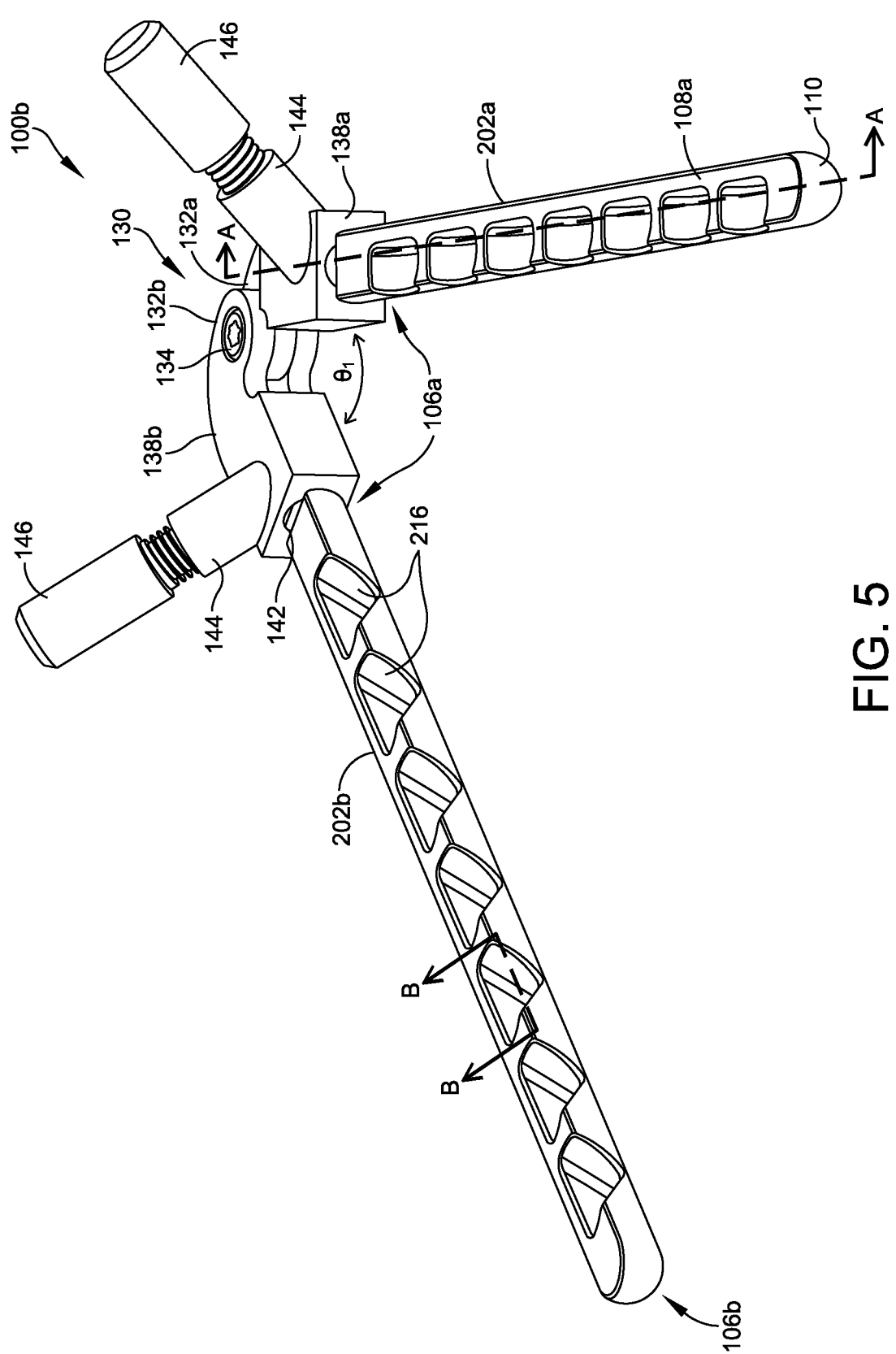
FIG. 5 illustrates an isometric view of an adjustable surgical guide including a plurality of scallop guides, in accordance with some embodiments.
Figure 6:
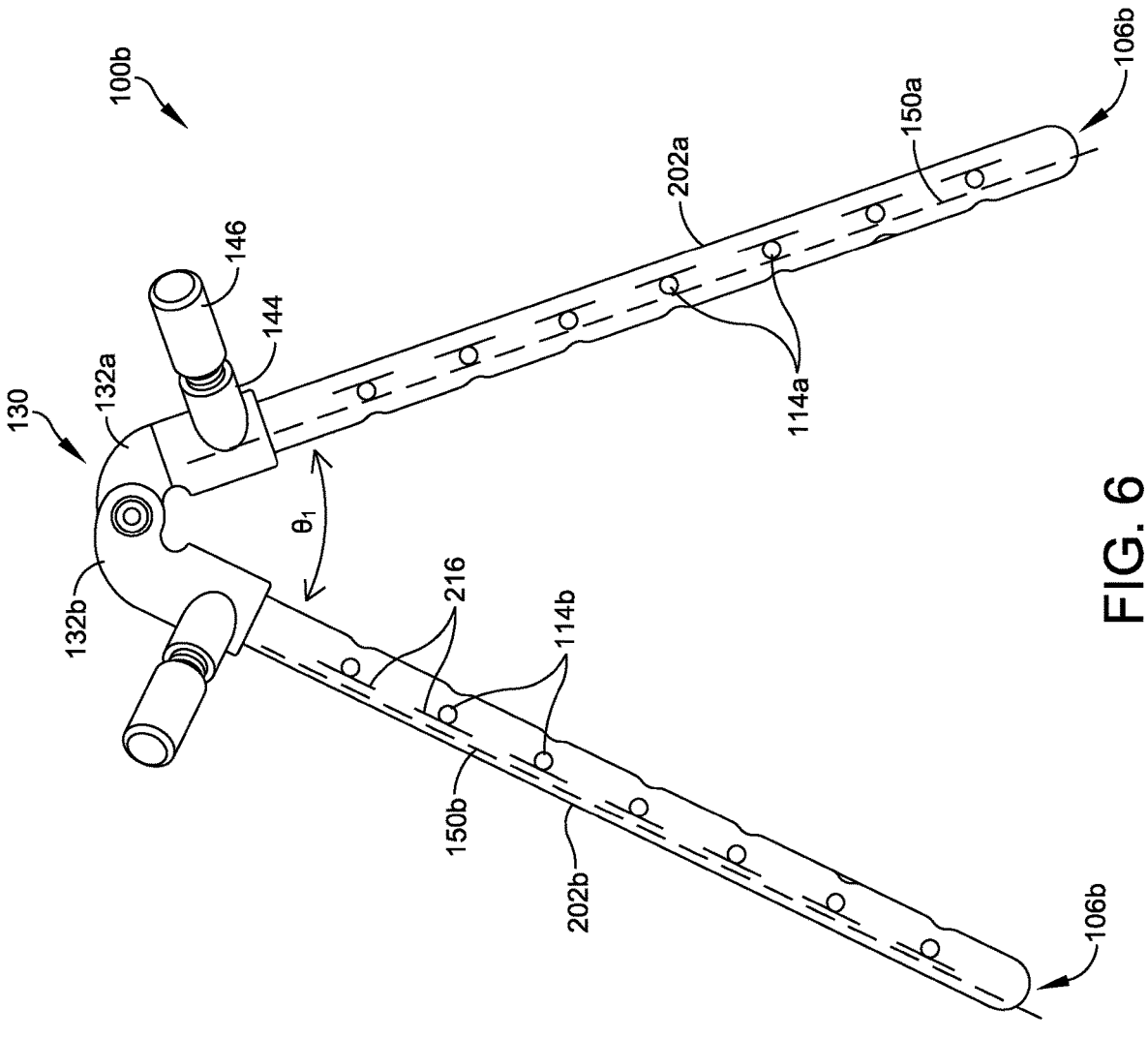
FIG. 6 illustrates a top view of the adjustable surgical guide of FIG. 5, in accordance with some embodiments.
Figure 7:
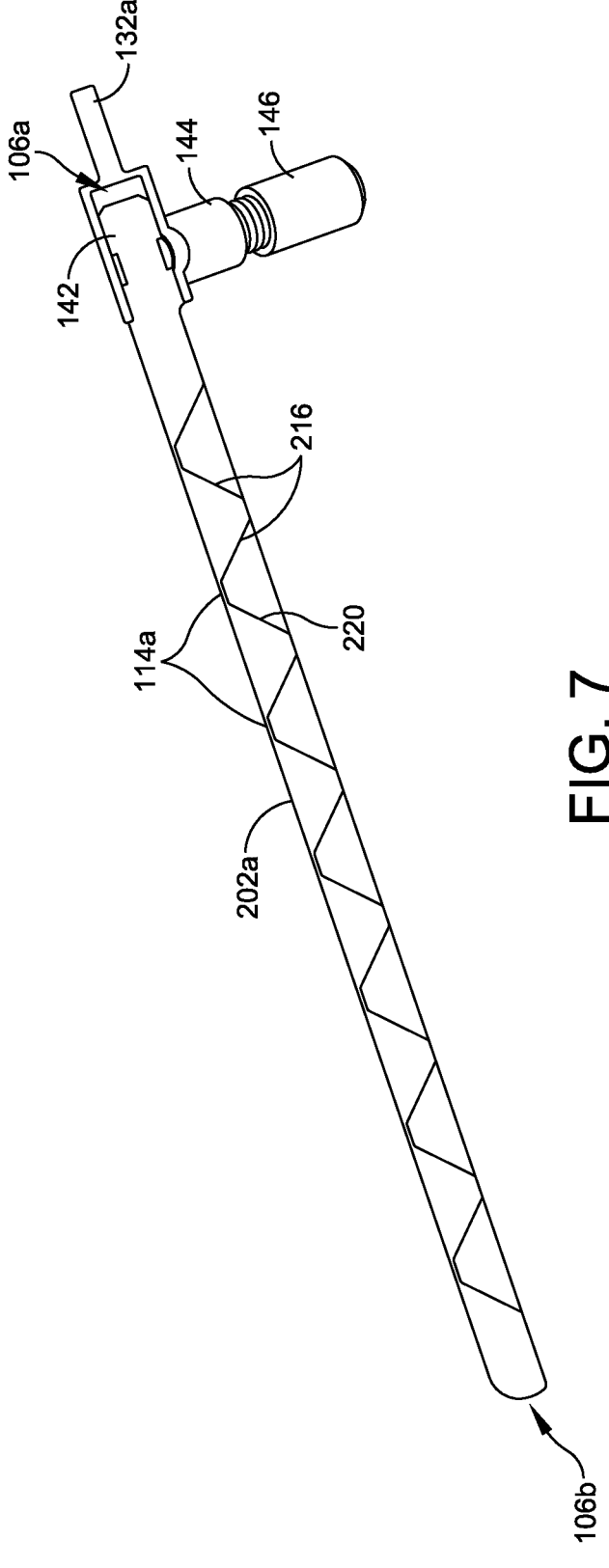
FIG. 7 illustrates a cross-sectional view of the adjustable surgical guide of FIG. 5 taken along line A-A, in accordance with some embodiments.
Figure 8:
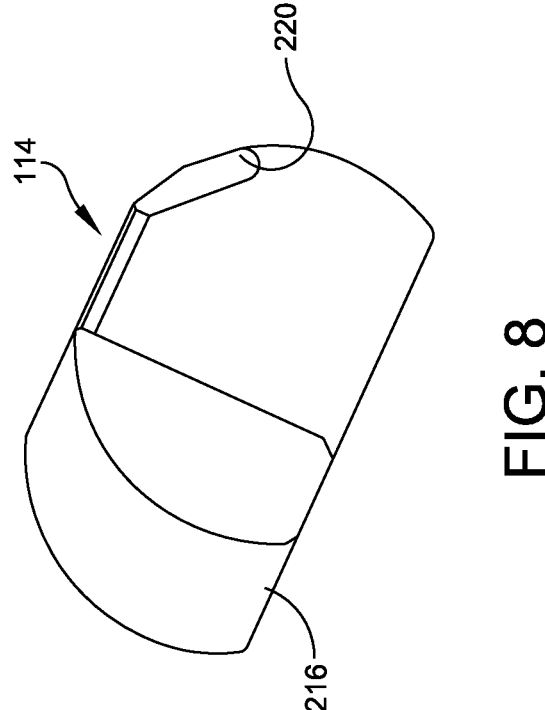
FIG. 8 illustrates a cross-sectional view of a scallop guide of the adjustable surgical guide of FIG. 5 taken along line B-B, in accordance with some embodiments.

As shown in FIG. 4, in some embodiments, the locking element 144 includes a threaded shaft 154 extending from an unthreaded head 156. The locking element 144 can be tightened and/or locked against the surface of the guide arm 102a, 102b to maintain the guide arm 102a, 102b in a fixed position with respect to the guide connection portion 138a, 138b. For example, in the illustrated embodiment, the threaded shaft 154 is rotatably interfaced with the internal threads of the channel 153 to tighten the locking element 144 against a respective guide arm 102a, 102b, although it will be appreciated that any suitable locking mechanism 143, such as a permanent and/or fixed locking mechanism, can be used to couple the guide arms 102a, 102b to respective guide connection portions 138a, 138b. In other embodiments, the pivot arms 132a, 132b are formed integrally with the guide arms 102a, 102b.

In use, and as described in greater detail below, the adjustable surgical guide 100a is configured to guide insertion of a one or more guide elements, such as a k-wire, into the least one bone. A cut can be formed in a bone using one or more guide holes 114a, 114b and/or additional cutting guides coupled to one or more guide elements. For example, in some embodiments, a first guide arm 102a of the adjustable surgical guide 100a is positioned adjacent to a bone to position a first guide element in the bone. The guide element can include any suitable guide element, such as, for example, a k-wire. The guide element can be positioned based on pre-operative imaging, simultaneous imaging, and/or using any other method.

After coupling the first guide arm 102a to the bone, an angle $\Theta_1$ between the first guide arm 102a and the second guide arm 102b can be adjusted to position the second guide arm 102b at predetermined position on the bone. For example, in some embodiments, the angle $\Theta_1$ between the first guide arm 102a and the second guide arm 102b can be adjusted to any suitable angle within a predetermined range of angles, such as, for example, between 0-90°, 0-180°, 0-270°, 0-360°, and/or any other suitable range of angles. A second guide element is inserted through at least one hole 122b extending through the second guide arm 102b.

After coupling the guide elements to the bone, and as described in greater detail below, the adjustable surgical guide 100a is removed from the surgical site and at least one cutting guide is coupled to one or more of the first guide element and the second guide element. A cutting instrument, such as a burr, saw, etc., may be positioned through the cutting guide and one or more cuts formed in the bone. In some embodiments, the adjustable surgical guide includes one or more openings sized and configured to guide the cutting instrument to a predetermined position and/or within a predetermined area of the bone. The cutting instrument forms a cut in the bone, for example, to form a wedge cut, osteotomy, and/or other cut in the bone. In some embodiments, the one or more openings include a slot sized and configured to position a blade or other cutting instrument along a predetermined axis to form a resection cut in the bone.

FIGS. 5-8 illustrates an embodiment of an adjustable surgical guide 100b including guide arms 202a, 202b defining a plurality of scallop guides 216, in accordance with some embodiments. The adjustable surgical guide 100b is similar to the adjustable surgical guide 100a discussed in conjunction with FIGS. 1-4, and similar description is not repeated herein. Each of the guide arms 202a, 202b of the adjustable surgical guide 100b includes a plurality of scallop guides 216 sized and configured to position a guide element within a hole 114a, 114b defined in the center of each of the scallop guides 216.

In some embodiments, each of the scallop guides 216 includes an inner surface 220 defining a sloped, or scalloped, funnel. A guide hole 114a, 114b is positioned at the apex (or lowest point) of the sloped inner surface 220. In some embodiments, the inner surface 220 is configured to control motion of a surgical instrument, such as, for example, a burr inserted through a guide hole 114a, 114b. In the illustrated embodiment, the scallop guides 216 formed in the first guide arm 202a are aligned with the scallop guides 216 formed in the second guide arm 202b. It will be appreciated that each of the guide arms 202a, 202b can include a greater or lesser number of scallop guides 216 aligned with and/or offset from scallop guides 216 in the other of the guide arms 202a, 202b.

Figure 9:
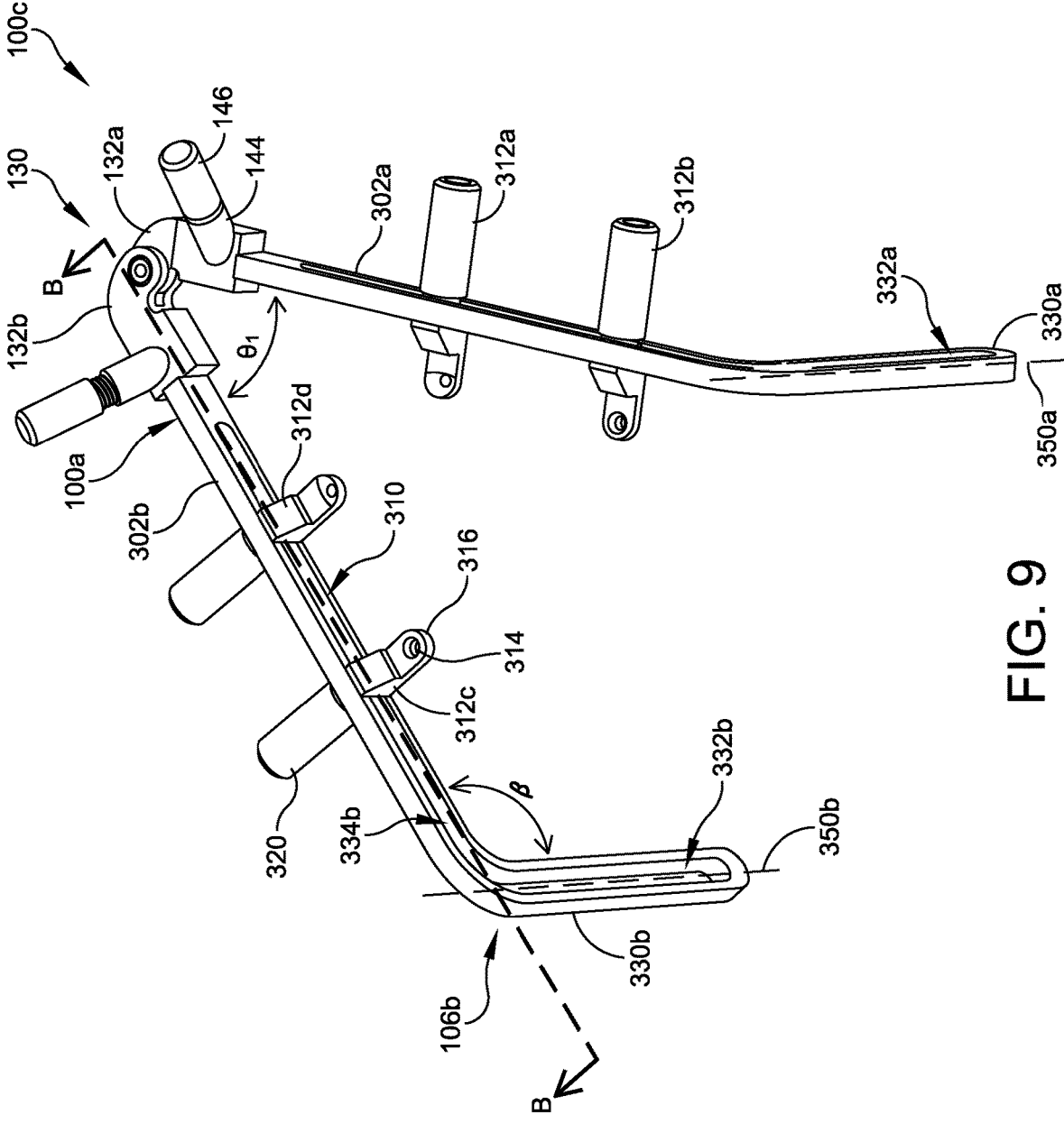
FIG. 9 illustrates an isometric view of an adjustable surgical guide including guide arms defining adjustment slots, in accordance with some embodiments.
Figure 10:
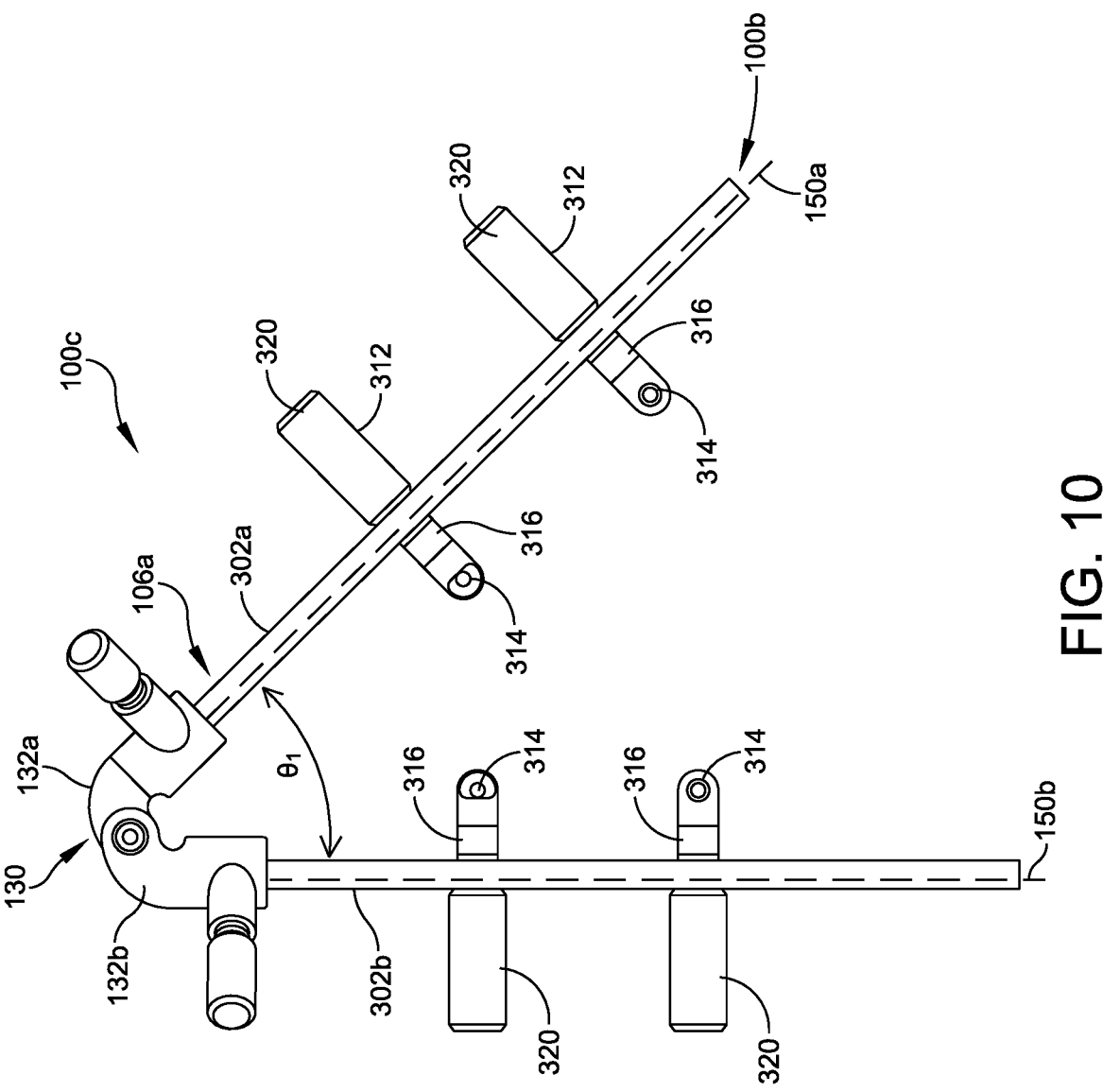
FIG. 10 illustrates a top view of the adjustable surgical guide of FIG. 9, in accordance with some embodiments.
Figure 11:
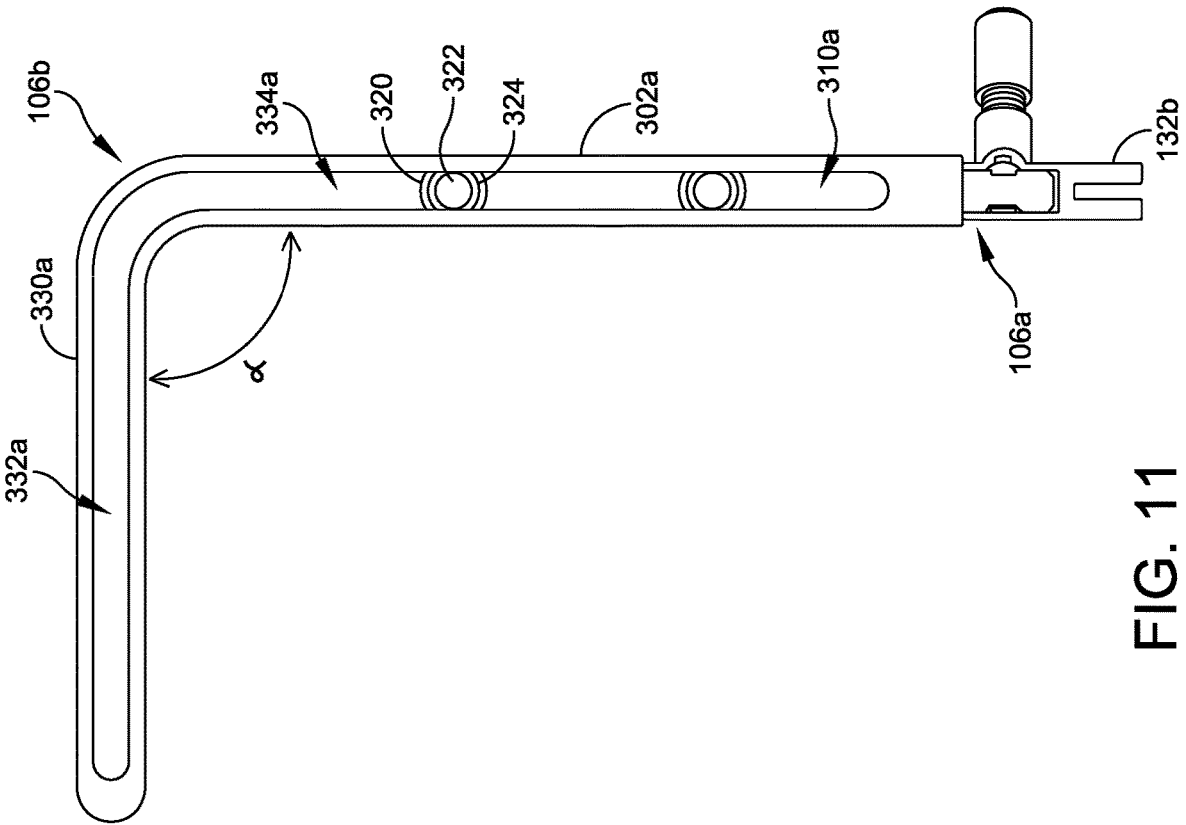
FIG. 11 illustrates a cross-sectional view of a guide arm of the adjustable surgical guide of FIG. 9 taken along line A-A, in accordance with some embodiments.
Figure 12:
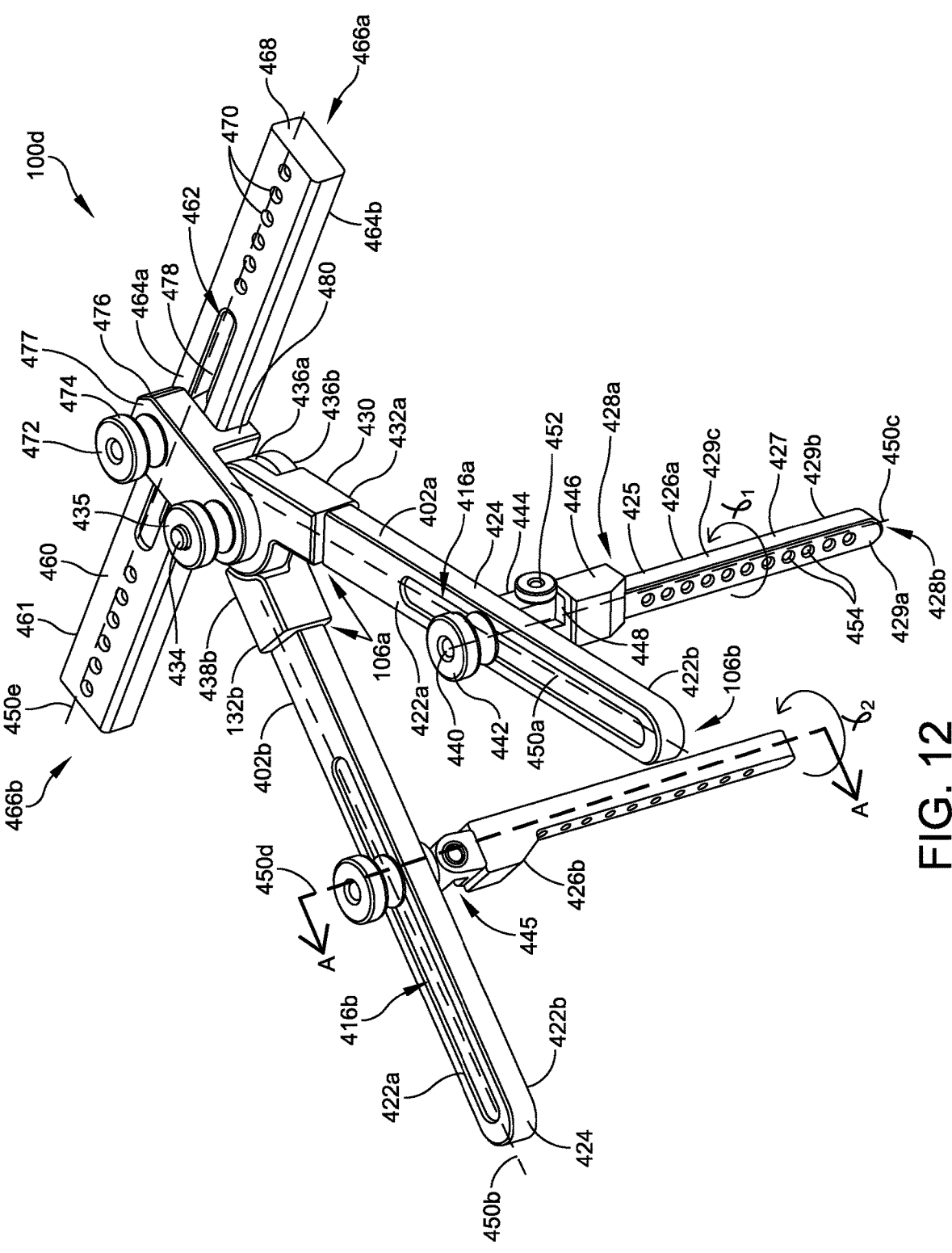
FIG. 12 illustrates an adjustable surgical guide including multiple position and angle adjustments, in accordance with some embodiments.
Figure 13:
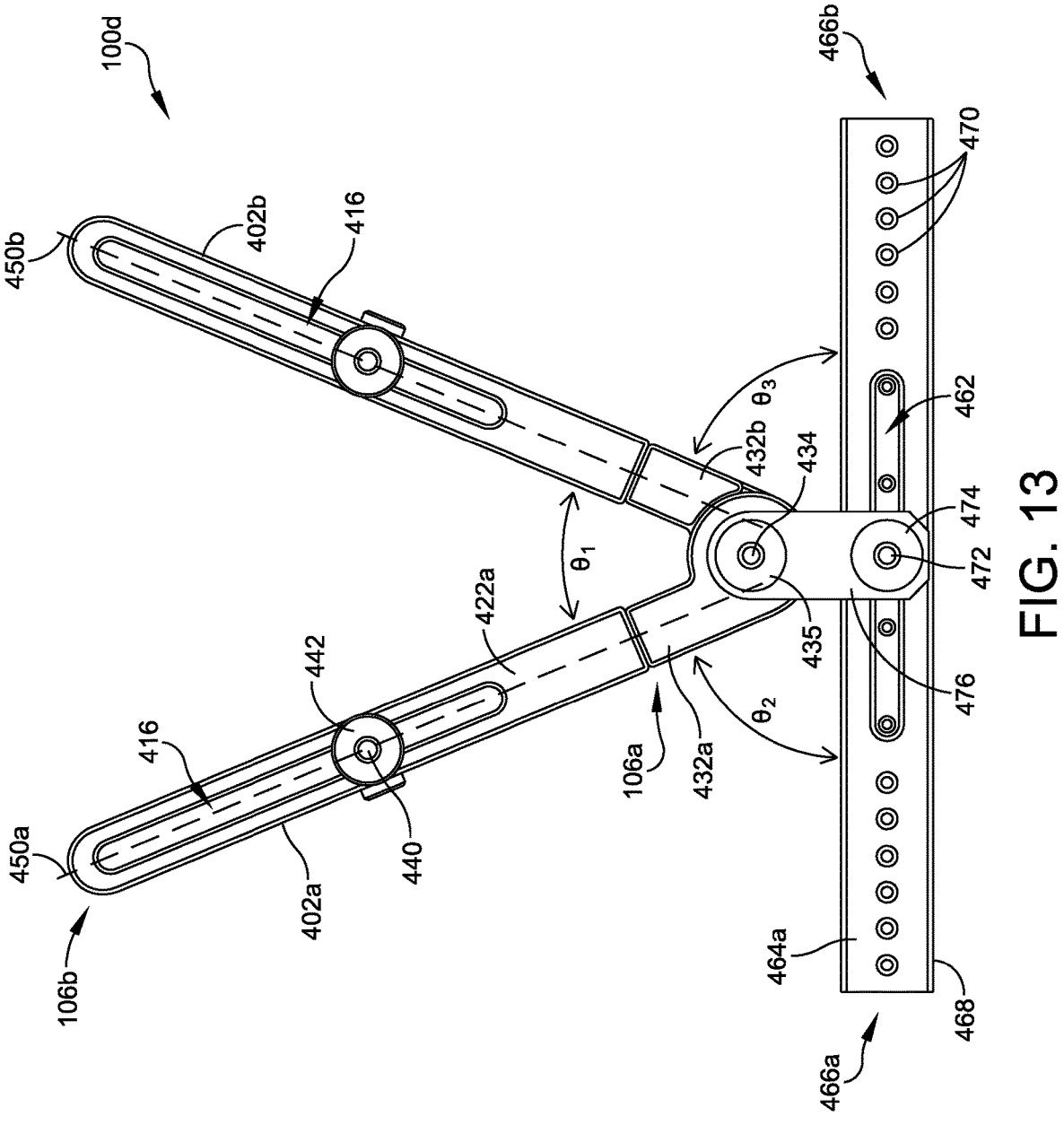
FIG. 13 illustrates a top view of the adjustable surgical guide of FIG. 12, in accordance with some embodiments.
Figure 14:
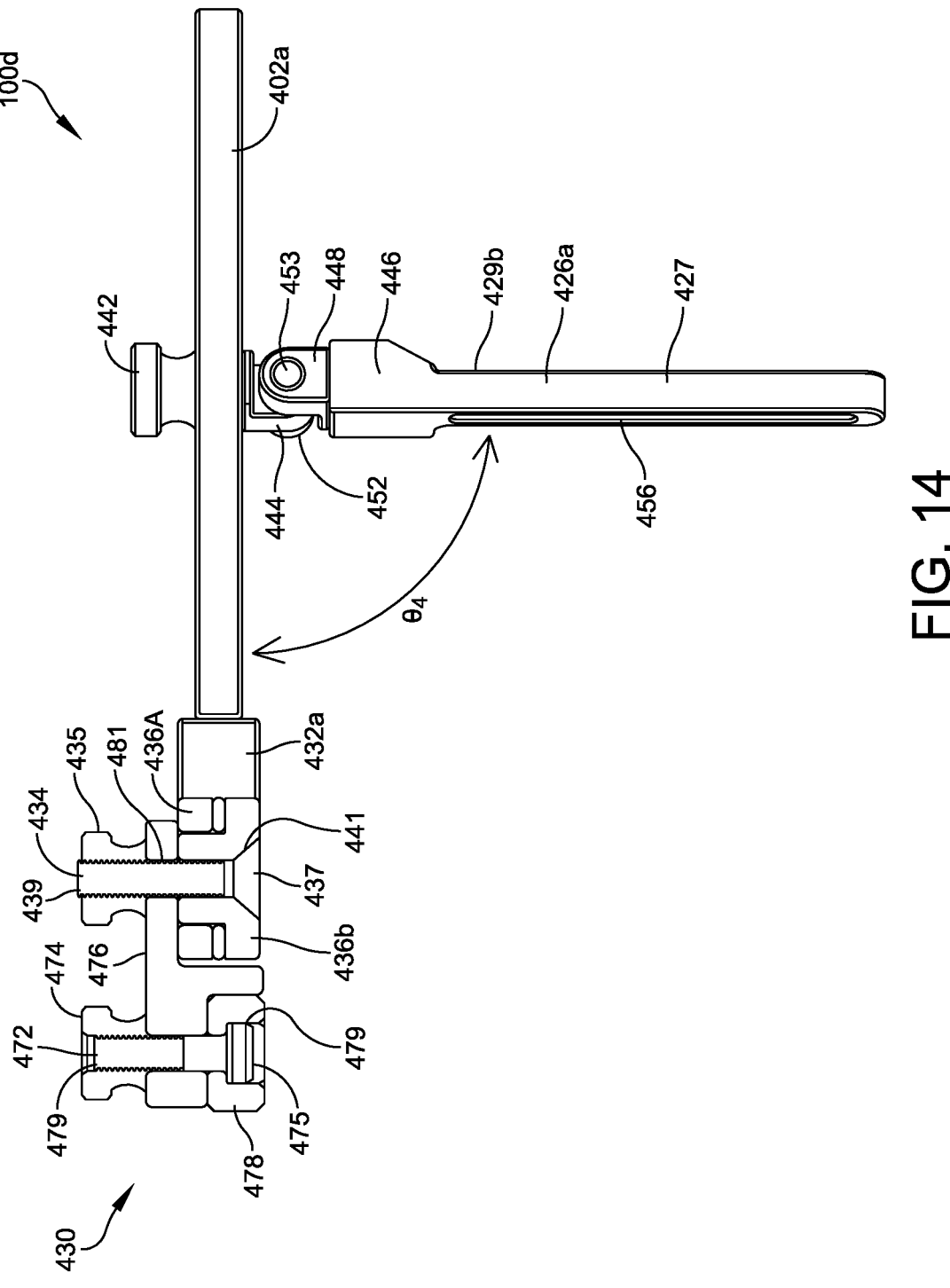
FIG. 14 illustrates a side view of the adjustable surgical guide of FIG. 12, in accordance with some embodiments.
Figure 15:
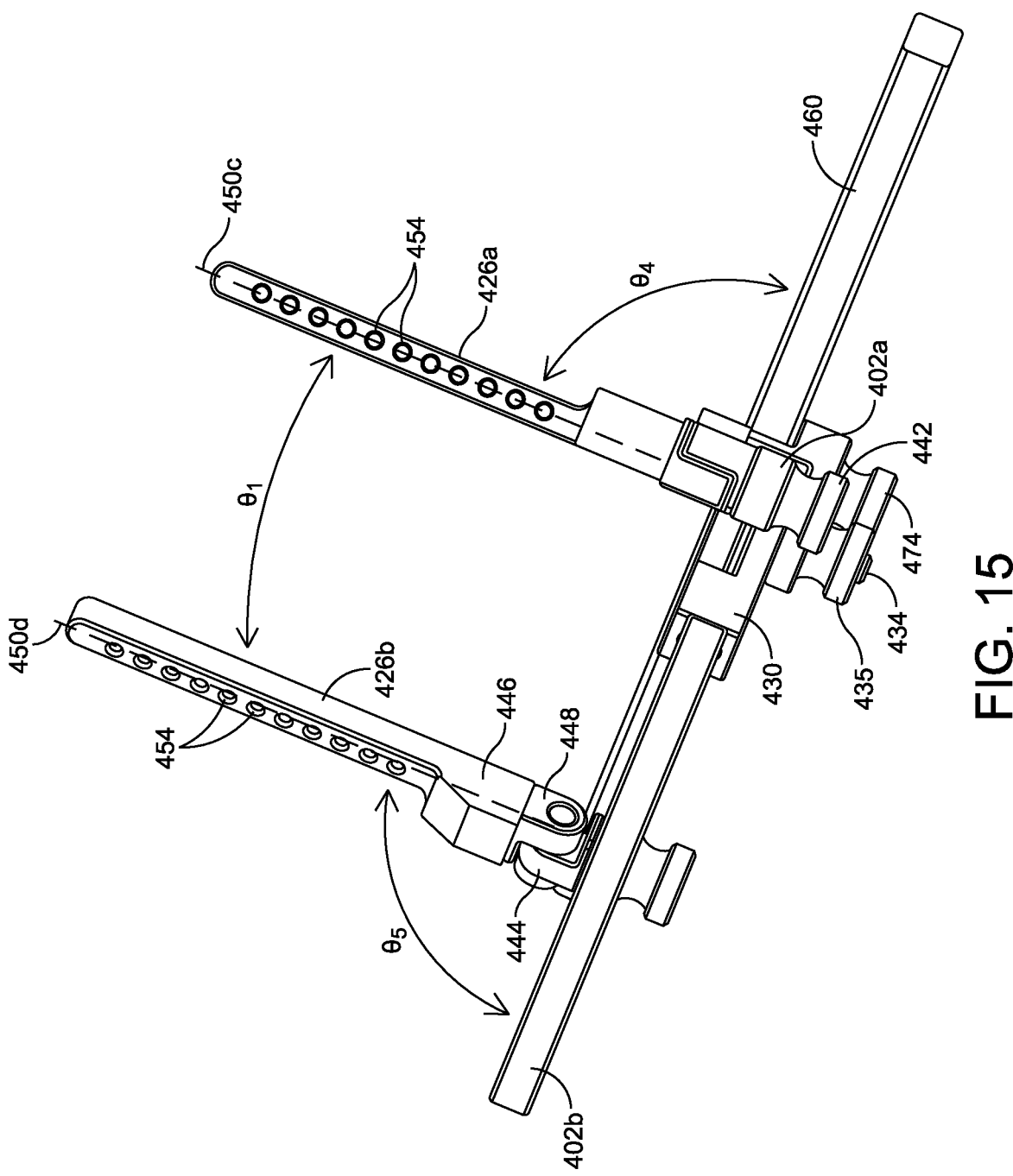
FIG. 15 illustrates a distal view of the adjustable surgical guide of FIG. 12, in accordance with some embodiments.
Figure 16:
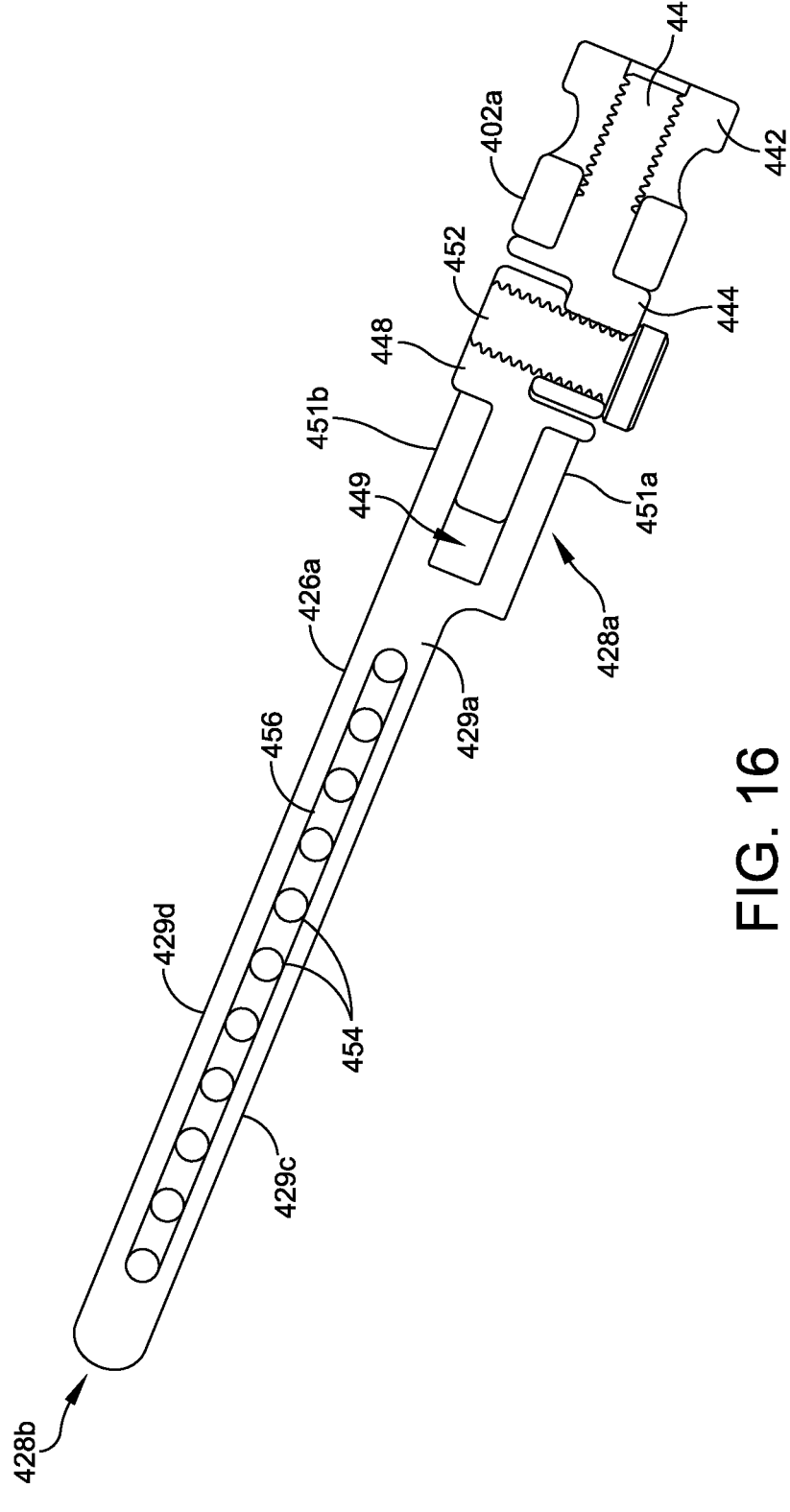
FIG. 16 illustrates a cross-sectional view of the adjustable surgical guide of FIG. 12 taken along line A-A, in accordance with some embodiments.

FIGS. 9-11 illustrate an embodiment of an adjustable surgical guide 100c including first and second guide arms 302a, 302b each defining slots 310a, 310b sized and configured to receive one or more sliding guide elements 312a-312d therein, in accordance with some embodiments. The adjustable surgical guide 100c is similar to the adjustable surgical guide 100a discussed in conjunction with FIGS. 1-4, and similar description is not repeated herein. In some embodiments, each of the guide arms 302a, 302b defines a slot 310a, 310b extending substantially along the longitudinal axis 150a, 150b of the respective guide arm 302a, 302b. In the illustrated embodiment, the slot 310a, 310b extends substantially from a proximal end 106a of each guide arm 302a, 302b to a distal end 106b of each guide arm 302a, 302b, although it will be appreciated that the slots 310a, 310b can extend over any portion of the respective guide arm 302a, 302b and is within the scope of this disclosure.

In some embodiments, each slot 310a, 310b is sized and configured to receive one or more sliding guide elements 312a-312d therein. Each of the sliding guide elements 312a-312d include a guide portion 316 coupled to a locking portion 320. The guide portion 316 includes an extension 322 (see FIG. 11) sized and configured to extend through a slot 310a, 310b of the respective guide arm 302a, 302b. The locking portion 320 is coupled to the extension 322. In some embodiments, the locking portion 320 is configured to maintain the sliding guide element 312a-312d in a fixed position within the slot 310a, 310b. For example, in some embodiments, the guide portion 316 of each of the sliding guide elements 312a0-312d includes a first surface configured to abut the respective guide arm 302a, 302b on a first side. The locking portion 320 includes a second surface configured to abut the respective guide arm 302a, 302b on a second side. When the locking portion 320 is tightened to the guide portion 316 (for example, by rotating the locking portion 320 to engage threads formed on the extension 322), the first and second surfaces form a friction lock that prevents movement of the slideable guide element 312a-312d within the slot 310a, 310b.

In some embodiments, the guide portion 316 defines a guide hole 314 extending therethrough. The guide hole 314 is sized and configured to receive a guide element, a cutting element, and/or any other suitable element therethrough. For example, in some embodiments, at least one guide hole 314 is sized and configured to receive a guide element such that the guide element is coupled to a bone at a predetermined location. In some embodiments, a guide element and/or a cutting element may be inserted through a guide hole and the sliding guide element 312a-312d may be subsequently traversed through the slot 310a, 310b to select a position for insertion with respect to the bone along an axis parallel to the axis of the guide arm 302a, 302b and/or the slot 310a, 310b.

In some embodiments, one or more of the guide arms 302a, 302b includes a second guide portion 330a, 330b extending along a longitudinal axis 350a, 350b disposed at a predetermined angle $\alpha$, $\beta$ with respect to the longitudinal axis 150a, 150b of the respective guide arm 302a, 302b. For example, in the illustrated embodiment, each of the guide arms 302a, 302b includes a second guide portion 330a, 330b extending along a third longitudinal axis 350a and a fourth longitudinal axis 350b, respectively, each positioned at an angle of about 90° with respect to the respective first or second longitudinal axis 150a, 150b. The second guide portion 330 defines a second slot 332a, 332b sized and configured to receive a sliding guide element 312a-312d therein. The second slot 332a, 332b is configured to guide the sliding guide element 312a-312d along the third or fourth longitudinal axis 350a, 350b. For example, in some embodiments, the second slot 332a, 332b positions a sliding guide element 312a-312d such that a guide element can be located within the bone at an angle $\alpha$, $\beta$ with respect to a guide element positioned within the bone by a sliding guide element 312a-312d positioned within the first slot 310a, 310b.

In some embodiments, the first slot 310a, 310b and the second slot 332a, 332b are coupled to form a continuous adjustment slot 334a, 33b configured to allow continuous movement of a slideable guide element 312a-312b along a first axis 150a, 150b and/or a second axis 350a, 350b depending on the position of the slideable guide element 312a-312d within the continuous adjustment slot 334. Although embodiments are illustrated with a single continuous adjustment slot 334a, 334b including a first slot 310a, 310b and a second slot 332a, 332b, it will be appreciated that the guide arms 302a, 302b can define any number of continuous and/or discrete slots.

FIGS. 12-16 illustrate an adjustable surgical guide 100d including multiple position and angle adjustments, in accordance with some embodiments. The surgical guide 100d is similar to the surgical guides 100a, 100b, 100c discussed in conjunction with FIGS. 1-11, and similar description is not repeated herein. The surgical guide 100d includes a first extension arm 402a having a first guide arm 426a extending therefrom and a second extension arm 402b having a second guide arm 426b extending therefrom. The first extension arm 402a and the second extension arm 402b are coupled by a pivot element 430. As discussed above with respect to the surgical guide 100a, the pivot element 430 is configured to adjust a first angle $\Theta_1$ in a first plane between the first extension arm 402a (or the first guide arm 426a) and the second extension arm (or the second guide arm 426b). As discussed in greater detail below, in some embodiments, the pivot element 430 is configured to adjust a second angle $\Theta_2$ between the first extension arm 402a and a lateral adjustment arm 460 and a third angle $\Theta_3$ between the second extension arm 402b and the lateral adjustment arm 460 in the first plane.

Each of the extension arms 402a, 402b includes a body 422 extending substantially along a first longitudinal axis 450a or a second longitudinal axis 450b, respectively. The body 422 extends between an upper surface 422a and a lower surface 422b and is defined by a side wall 424. Each extension arm 402a, 402b defines a slot 416a, 416b extending from the upper surface 422a through the body 422 to the lower surface 422b. Each slot 416a, 416b is sized and configured to receive a threaded connector 440 of a respective guide arm 426a, 426b, therethrough. Each of the extension arms 402a, 402b include a proximal portion sized and configured to couple to a respective guide connection portion 438a, 438b of the pivot element 430. The extension arms 402a, 402b can be retained within the guide connection portion 438a, 438b using any suitable retention mechanism, such as a friction retention, a threaded retention, the use of tightening element, and/or any other suitable retention mechanism.

In some embodiments, a guide arm 426a, 426b is slideably coupled to a respective one of the extension arms 402a, 402b. Each of the guide arms 426a, 426b extend from a proximal end 428a to a distal end 428b. The first guide arm 426a extends substantially along a third longitudinal axis and the second guide arm 426b extends substantially along a fourth longitudinal axis 450d. The guide arms 426a, 426b each include a body 425 extending between a first surface 429a and a second surface 429b and defined by a sidewall 427. A plurality of guide holes 454 extend from the first surface 429a to the second surface 429. In the illustrated embodiments, each of the guide holes 454 extends along an axis that is perpendicular to the longitudinal axis 450c, 450d of the respective guide arm 426a, 426b, although it will be appreciated that the guide holes 454 can extend through the guide arms 426a, 426b at any suitable angle and are within the scope of this disclosure. Although the guide holes 454 are illustrated extending from a first surface 429a to a second surface 429b, it will be appreciated that the guide holes 454 can also extend from a third surface 429c to a fourth surface 429b.

In some embodiments, each guide arm 426a, 426b is coupled to a respective extension arm 402a, 402b by a pivoting slide element 445. The pivoting slide element 445 includes a pivot element 445 comprising a first pivot connector 448 formed integrally with a proximal end 446 of the guide arms 426a, 426b and a second pivot connector 444 comprising a connection extension 440 sized and configured to extend through the slot 416a, 416b. The first pivot connector 448 is coupled to the second pivot connector 444 by a pivot pin 452 extending through holes formed in each of the pivot connectors 444, 448. In some embodiments, the pivot element 445 allows adjustment of an angle $\Theta_4$, $\Theta_5$ between a guide arm 426a, 426b and a respective one of the extension arms 402a, 402b in a plane defined by the longitudinal axis 450a, 450b of the respective extension arm 402a, 402b and the longitudinal axis 450c, 450d of the respective guide arm 426a, 426b. In various embodiments, the angles $\Theta_4$, $\Theta_5$ can be any angle within a predetermined range of angles, such as, for example, any angle within a range of 0°-90°, 0°-180°, 45°-90°, and/or any other suitable range of angles.

In some embodiments, each of the pivot elements 445 includes a connection extension 440 extending through the slot 416a, 416b. The connection extension 440 is configured to slideably couple the guide arm 426a, 426b to the respective extension arm 402a, 402b. For example, in the illustrated embodiment, the connection extension 440 includes a threaded shaft extending from the second pivot connector 444. The threaded shaft is configured to threadably couple to internal threads of a locking element 442. The locking element 442 is threaded onto the threaded shaft and maintains the connection extension 440 within the slot 416a, 416b. The position of the guide arm 426a, 426b along a longitudinal axis 450a, 450b defined by the respective extension arm 402a, 402b can be adjusted by sliding the connection extension 440 within the slot 416a, 416b. In some embodiments, the locking element 442 can be tightened to lock the position of the targeting arm 426a, 426b within the slot 416.

In some embodiments, each guide arm 426a, 426b is configured to rotate about the respective longitudinal axis 450c, 450d of the guide arm 426a, 426b. For example, in the illustrated embodiment, the second pivot connector 444 includes a threaded connection extension 440 extending through the slot 416. The locking element 442 can be loosened to allow rotation of the guide arm 426a, 426b about the respective longitudinal axis 450c, 450d. After setting an angle of rotation of the guide arm 426a, 426b, the locking element 442 is tightened to fix the rotational position of the guide arm 426a, 426b at the selected angle of rotation $\gamma_1$, $\gamma_2$. The angle of rotation $\gamma_1$, $\gamma_2$ can include any suitable angle of rotation, such as, for example, any angle between 0°-360°. In some embodiments, the selected angle of rotation $\gamma_1$, $\gamma_2$ can be adjusted by rotating each of the guide arms 426a, 426b with respect to the pivot element 445 such that the selected angle of rotation $\gamma_1$, $\gamma_2$ of the guide arms 426a, 426b can be adjusted to position the guide arms 426a, 426b at any angular position with respect to the pivot element 445. Although embodiments are discussed herein including rotatable guide arms 426a, 426b, it will be appreciated that the guide arms 426a, 426b can have a fixed rotational orientation with respect to the extension arms 402a, 402b, in some embodiments.

In some embodiments, the adjustable surgical guide 100d includes a lateral adjustment arm 460 including a body 461 extending substantially along a fifth longitudinal axis 450e from a first end 466a to a second end 466b. The body 461 extends between a first surface 464a and a second surface 464b and is defined by a perimeter wall 468. In some embodiments, one or more guide holes 470 extend through the body 461 from the first surface 464a to the second surface 464b. The guide holes 470 are sized and configured to receive a guide element and/or any other suitable element therethrough. The lateral adjustment arm 460 is configured to provide lateral movement of the pivot element 430 and the extension arms 402a, 402b parallel to the fifth axis 450e.

For example, in some embodiments, the pivot element 430 is coupled to the lateral adjustment arm 460 by a lateral adjustment component 476. The lateral adjustment component 476 includes a body 477 configured to slideably contact the first surface 464a of the longitudinal adjustment arm 460. A slide element 478 is coupled to the body 477 and is configured to maintain the body 477 in contact with the first surface 464a. The slide element 478 can be positioned within a slot 462 defined in the lateral adjustment arm 460 and/or in contact with the second surface 464b of the lateral adjustment arm 460.

In some embodiments, a pivot connector 480 extends from the body 477. The pivot connector 480 defines a pivot pin hole 481 sized and configured to receive the pivot pin 434 therethrough. The pivot pin 434 couples the pivot element 430 to the lateral adjustment component 476. For example, in the illustrated embodiment, the pivot pin 434 extend through the pivot pin hole 481 and is coupled to the locking element 435.

In some embodiments, the slide element 478 can be moved laterally within the slot 462 to move the pivot element 430 and, by extension, the extension arms 402a, 402b. In some embodiments, the slide element 478 is coupled to the body 477 by a locking pin 472 having a head 457 in contact with the slide element 478 and a shaft 479 extending through the body 477 of the lateral adjustment component 476. A locking element 474 defines an internal channel 481 having internal threads configured to engage the threads of the locking pin 472 to fix the position of the slide element 478 within the slot 462.

In some embodiments, the pivot pin 434 is configured to allow rotation of the pivot element 430 to adjust a second angle $\Theta_2$ between the first extension arm 402a (or first guide arm 426a) and the horizontal adjustment arm 460 and a third angle $\Theta_3$ between the second extension arm 402b (or second guide arm 426b) and the horizontal adjustment arm 460. For example, in some embodiments, the locking element 435 can be loosened with respect to the pivot pin 434 such that the pivot element 430 is able to rotate about the pivot pin 434 with respect to the pivot connector 480. Rotational movement of the pivot element 430 adjusts the second angle $\Theta_2$ between the first extension arm 402a and the lateral adjustment arm 460 and the third angle $\Theta_3$ between the second extension arm 402b and the lateral adjustment arm 460 while maintaining the first angle $\Theta_1$ between the first and second extension arms 402a, 402b. Although embodiments are illustrated with a rotatable pivot element 430, it will be appreciated that the rotational angle of the pivot element 430 may be fixed with respect to the pivot connector 480 and adjustments of the angles $\Theta_1$, $\Theta_2$, and $\Theta_3$ may be accomplished solely by movement of the extension arms 402a, 402b with respect to each other.

FIG. 17 illustrates a method 500 of forming a cut in a bone, in accordance with some embodiments. At step 502, an adjustable surgical guide 100d is positioned adjacent to a bone. Although embodiments are discussed herein with respect to the adjustable surgical guide 100a-100d, it will be appreciated that any of the surgical guides 100a-100d discussed above can be used in conjunction with the method 500 and such use is within the scope of this disclosure. In some embodiments, an adjustable surgical guide 100a includes a first guide arm 102a extending substantially on a first longitudinal axis 150a and defining a first plurality of openings 114a, a second guide arm 102b extending substantially on a second longitudinal axis 150b and defining a second plurality of openings 114b, and a pivot element 130 coupling the first guide arm 102a to the second guide arm 102b. In some embodiments, a temporary fixation element, such as a k-wire, may be inserted through a hole defined through the pivot element 130, such as a hole extending through a pivot pin 134, to maintain the adjustable surgical guide 100a at a predetermined position with respect to the bone.

At optional step 504, a first guide element is inserted through a selected one of the first plurality of openings 122a defined by the first guide arm 102a. For example, in some embodiments, a first guide element, such as a k-wire, is inserted through a selected one of the holes 122a defined in the first guide arm 102a. The first guide element can be coupled to a bone, for example, prior to and/or after insertion of the first guide element through the selected one of the plurality of holes 122a to define a first reference point for a wedge osteotomy to be formed in the bone.

At optional step 506, the first guide arm 102a and the second guide arm 102b are pivoted about the pivot element 130 to adjust the angle $\Theta_1$ between the first guide arm 102a and the second guide arm 102b within the first plane. In some embodiments, pivoting the first guide arm 102a and the second guide arm 102b includes increasing and/or decreasing the first angle $\Theta_1$ between the first guide arm 102a and the second guide arm 102b to define the width of a wedge osteotomy to be formed in a bone.

At optional step 508, a longitudinal position of a first guide arm 426a, a second guide arm 426b, and a pivot element 430 is adjusted along a third longitudinal axis 450e. For example, in some embodiments, the adjustable surgical guide 100d includes a lateral adjustment arm 460 defining a slot 462. The slot is configured to receive a slide element 478 therein. The slide element 478 is coupled to the pivot element 430 and is configured to move the pivot element 430 laterally along the third longitudinal axis 450e. In some embodiments, the lateral adjustment arm 460 is coupled to the bone by a third guide element prior to and/or subsequent to adjusting the lateral position of the pivot element 430.

At optional step 510, a longitudinal position of the first guide arm 426a and/or the second guide arm 426b is adjusted with respect to the pivot element 430. For example, in some embodiments, each of the first guide arm 426a and the second guide arm 426b include a slide element 440 disposed through a slot 416 defined by a respective extension arm 402a, 402b coupled to the pivot element 430. Each of the extension arms 402a, 402b and the corresponding slot 416 extend substantially along a longitudinal axis 450a, 450b. In some embodiments, a locking element 442 is coupled to the slide element 440 and can be tightened to fix the position of the guide arm 426a, 426b within the slot 416 and/or can be loosened to allow adjustment of the guide arm 426a, 426b within the slot 416.

At optional step 512, an angle of the first guide arm 426a and/or the second guide arm 426b is adjusted with respect to a pivot plane defined by the pivot element 430. For example, in some embodiments, the first guide arm 426a comprises an angular pivot element 444 configured to selectively adjust the angle between the longitudinal axis 450c of the first guide arm 426a or the longitudinal axis 450d of the second guide arm 426b and the pivot plane. In some embodiments, the pivot plane includes a plane defined by the longitudinal axes 450a, 450b of the guide arm connectors 432a, 432b of the pivot element 430.

At optional step 514, a second guide element is inserted through a selected one of the second plurality of openings 122b defined by the second guide arm 102b. For example, in some embodiments, a second guide element, such as a k-wire, is inserted through the selected one of the holes 122b defined in the second guide arm 102b. The second guide element is coupled to a bone to define a second point of reference for a wedge osteotomy to be formed in the bone.

At step 516, a cutting guide is inserted through one or more of the guide holes 114a, 114b, 214, 454, extending through a portion of the adjustable surgical guide. The cutting instrument, such as a burr, is sequentially inserted into the one or more guide holes 114a, 114b, 214, 454 to form a wedge osteotomy in the bone. In some embodiments, a cut may be formed in the bone by pivoting and/or rotating the cutting instrument within a guide hole 114a, 114b, such as, for example. within a range of motion defined by a scallop guide 216.

Figure 18:
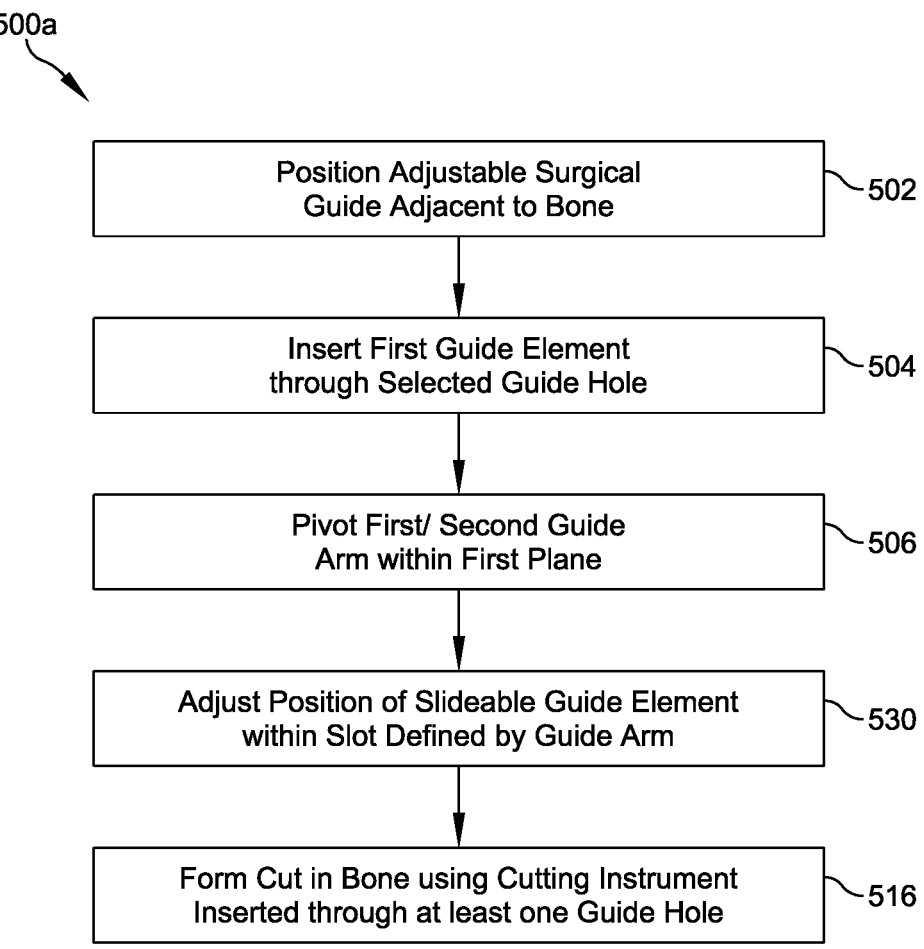
FIG. 18 is a flowchart illustrating a method of positioning an adjustable surgical guide, in accordance with some embodiments.

FIG. 18 illustrates a method 500a of forming a cut in a bone using an adjustable surgical guide having at least one slideable guide element, in accordance with some embodiments. Steps 502-506 of the method 500a are similar to steps 502-206 of the method 500 discussed above in conjunction with FIG. 17, and similar description is not repeated herein. At step 530, the position of at least one slideable guide element 312 within a slot 310 defined by one of a first guide arm 302a or a second guide arm 302b is adjusted. The slideable guide element 312 can include a locking element 320 that is loosened to allow movement of the slideable guide element 312 within the slot 310. After repositioning the slideable guide element 312, the locking portion 320 can be retightened to fix the position of the slideable guide element 312 within the slot 310. For example, in some embodiments, the guide portion 316 of each of the sliding guide elements 312 a first surface configured to abut the guide arm 302a, 302b on a first side. The locking portion 320 includes a second surface configured to abut the guide arm 302a, 302b on a second side. When the locking portion 320 is tightened to the guide portion 316 (for example, by rotating the locking portion 320 to engage threads formed on the extension 322), the first and second surfaces form a friction lock that prevents movement of the slideable guide element 312 within the slot 310. The method 500a proceeds to step 516 and continues through the method steps discussed above with respect to method 500.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A surgical guide, comprising: a first guide arm defining a first plurality of openings with a plurality of scallop guides sized and configured to guide a first guide element into a respective one of the first plurality of openings; a second guide arm defining a second plurality of openings; a pivot element coupling a first end of the first guide arm to a first end of the second guide arm such that an angular distance between the first guide arm and the second guide arm can be adjusted; an extension arm defining an adjustment slot; a lateral adjustment arm defining a slot extending substantially along a longitudinal axis; a slide element coupled to the pivot element so as to be received within the slot of the lateral adjustment arm, wherein the slide element is configured to provide movement of the pivot element; and a locking element coupled to the slide element, wherein the locking element is configured to selectively fix a position of the slide element within the slot of the lateral adjustment arm.

2. The surgical guide of claim 1, wherein the guide element defines a plurality of openings sized to receive a third guide arm.

3. The surgical guide of claim 2, wherein the first guide arm extends from a first slide element received within the adjustment slot.

4. The surgical guide of claim 2, wherein the first guide arm comprises an angular pivot element configured to selectively adjust an angular orientation of the first guide arm.

5. The surgical guide of claim 1 wherein each of the plurality of openings is defined in the center of each of the scallop guides.

6. The surgical guide of claim 5, wherein each scallop guide formed in the first guide arm is aligned with each scallop guides formed in the second guide arm.

7. The surgical guide of claim 5, wherein the number of scallop guides differs between the guide arms.

8. The surgical guide of claim 1, comprising a first guide block coupled to the first guide arm, the first guide block extending substantially parallel the first guide arm, wherein the first guide block defines a first subset of the first plurality of openings.

9. The surgical guide of claim 1, wherein the second guide arm defines a plurality of scallop guides sized and configured to guide a second guide element into a respective one of the second plurality of openings.

10. The surgical guide of claim 1, comprising a first locking element configured to releasably couple the first guide arm to the pivot element.

11. The surgical guide of claim 1, wherein each of the scallop guides includes an inner surface defining a sloped funnel.

12. The surgical guide of claim 11, wherein each opening is positioned at an apex of the sloped inner surface.

13. The surgical guide of claim 11, wherein inner surface is configured to control motion of a surgical instrument inserted through one of the plurality of openings.

14. A surgical guide, comprising: a first extension arm extending along a first longitudinal axis and defining a first slot defined between an upper surface of the first extension arm and a lower surface; a second extension arm extending along a second longitudinal axis and defining a second slot between an upper surface of the second extension arm and a lower surface; a pivot element coupling the first extension arm to the second extension arm such that a first angle between the first extension arm and the second extension arm is adjustable in a first plane; a first guide arm extending from a proximal end to a distal end and defining a first plurality of guide holes, the first guide arm slideably coupled to the first extension arm by a first connection extension received within the first slot such that a position of the first guide arm is adjustable along the first longitudinal axis; a second guide arm extending from a proximal end to a distal end and defining a second plurality of guide holes, the second guide arm slideably coupled to the second extension arm by a second connection extension received within the second slot such that a position of the second guide arm is adjustable along the second longitudinal axis; a lateral adjustment arm extending substantially along a third longitudinal axis, the lateral adjustment arm defining a third slot; a slide element coupled to the pivot element and received within the third slot, the slide element configured to provide lateral movement of the pivot element along the third longitudinal axis; and a locking element coupled to the slide element, the locking element configured to selectively fix a position of the slide element within the third slot.

15. The surgical guide of claim 14, wherein the first guide arm is coupled to the first extension arm by a first pivoting slide element including a first pivot connector formed integrally with the proximal end of the first guide arm; and a second pivot connector comprising the first connection extension, the second pivot connector coupled to the first pivot connector by a pivot pin, wherein the first pivoting slide element is configured to adjust an angle between the first guide arm and the first extension arm in a plane defined by the first longitudinal axis and a longitudinal axis of the first guide arm.

16. The surgical guide of claim 14, wherein the first guide arm is configured to rotate about a longitudinal axis of the first guide arm and a first locking element is configured to selectively fix a rotational position of the first guide arm at a selected angle of rotation.

17. The surgical guide of claim 14, wherein the lateral adjustment arm defines a plurality of guide holes extending from a first surface of the lateral adjustment arm to a second surface of the lateral adjustment arm, the guide holes sized and configured to receive a guide element therethrough.

18. The surgical guide of claim 14, wherein the pivot element is coupled to the lateral adjustment arm by a lateral adjustment component comprising a body configured to slideably contact a first surface of the lateral adjustment arm, a pivot connector extending from the body and defining a pivot pin hole sized and configured to receive a pivot pin coupling the pivot element to the lateral adjustment component, and wherein the pivot element is rotatable about the pivot pin to adjust a second angle between the first extension arm and the lateral adjustment arm and a third angle between the second extension arm and the lateral adjustment arm while maintaining the first angle between the first extension arm and the second extension arm.

\*　\*　\*　\*　\*